United States Patent [19]

Batt

[11] Patent Number: 4,833,164

[45] Date of Patent: May 23, 1989

[54] 2-SUBSTITUTED-1-NAPHTHOLS, PHARMACEUTICAL COMPOSITIONS OF, AND THEIR USE AS 5-LIPOXYGENASE INHIBITORS

[75] Inventor: Douglas G. Batt, Wilmington, Del.

[73] Assignee: E. I. Du Pont de Nemours and Company, Wilmington, Del.

[21] Appl. No.: 839,912

[22] Filed: Mar. 19, 1986

Related U.S. Application Data

[63] Continuation-in-part of Ser. No. 731,791, May 8, 1985, abandoned.

[51] Int. Cl.[4] .................... C07C 39/14; A61K 31/045
[52] U.S. Cl. ..................... 514/647; 568/27; 568/28; 568/31; 568/38; 568/63; 568/64; 568/736; 568/737; 564/84; 564/92; 564/180; 564/315; 560/17; 560/100; 560/255; 579/78; 579/497; 548/186; 548/235; 548/341; 548/551; 546/189; 546/344; 540/484; 514/319; 514/429; 514/510; 514/706; 514/708; 514/712; 514/717; 514/732; 514/885
[58] Field of Search ............. 568/736, 27, 28, 31, 568/38, 63, 64; 514/732, 319, 429, 510, 706, 708, 712, 717, 647; 548/551; 546/344

[56] References Cited

U.S. PATENT DOCUMENTS 3,761,526 9/1973 Houlihan et al. ............. 568/735
4,466,981 8/1984 Jones et al. ............. 424/311

FOREIGN PATENT DOCUMENTS 0146145 6/1985 European Pat. Off. .
0149588 7/1985 European Pat. Off. .
0190722 4/1986 European Pat. Off. .
60252441 5/1984 Japan .
60-036434 2/1985 Japan .
60-035436 2/1985 Japan .
1271132 4/1972 United Kingdom .
2072174 9/1981 United Kingdom .

OTHER PUBLICATIONS

Chemische Berichte, vol. 114, No. 3, 1981, pp. 1091–1098, Verlag Chemie, Weinheim, DE; F. Bohlmann et al.

Bagavant, G. et al., *Indian Journal of Pharmaceutical Sciences*, 1985, 47, pp. 12–15.

*Primary Examiner*—David B. Springer

[57] ABSTRACT

2-Substituted-1-naphthols are 5-lipoxygenase inhibitors which make them useful in the treatment of inflammation, obstructive lung diseases and/or psoriasis. Useful 2-substituent groups are alkyls, alkenyls, alkynyls, cycloalkyls, cycloalkenyls, the groups $CH_2-C\equiv C-(CH_2)_mR^5$ and $CH=CH-(CH_2)_nR^5$ (where m is 1–4, n is 0–3 and $R^5$ includes phenyl, $COOR^9$, where $R^9$ is H or alkyl of 1–4 carbons, $AR^6$ (where A is a methylene chain and $R^6$ is a variety of groups including Cl, Br, I, CHO, CN, $COOR^9$, $NH_2$, $SC(NH)NH_2$, phenyl, $P(O)(OR^9)_2$, etc.), and $CHR^7R^{21}$ (where $R^7$ is a variety of aromatic and heterocyclic groups and $R^{21}$ is H, optionally substituted phenyl and a variety of heterocyclic groups).

51 Claims, No Drawings

2-SUBSTITUTED-1-NAPHTHOLS, PHARMACEUTICAL COMPOSITIONS OF, AND THEIR USE AS 5-LIPOXYGENASE INHIBITORS

RELATIONSHIP TO OTHER APPLICATIONS

This application is a continuation-in-part of copending application Ser. No. 731,791, filed May 8, 1985, now abandoned.

BACKGROUND OF THE INVENTION

1. Field of Invention

This invention relates to 2-substituted-1-naphthols, and processes for their preparation, pharmaceutical compositions containing them and pharmaceutical methods using them.

2. Prior Art

U.S. Pat. No. 3,998,966 issued Dec. 21, 1976 to Fried and Harrison discloses 6-substituted 2-naphthyl acetic acid derivatives with antiinflammatory, analgesic, antipyretic and antipruritic activity.

U.S. Pat. No. 3,969,415 issued July 13, 1976 to E. G. Galantay discloses antiinflammatory 1(2-naphthyl)-2,3-butandien-1-ols of the formula

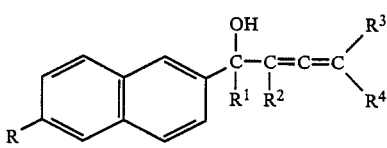

wherein R is H, Fl, Cl, Br, $C_1$-$C_4$ alkyl, $C_1$-$C_4$ alkoxy, $C_1$-$C_4$-alkylthio or difluoromethoxy, $R^1$ is H or $C_1$-$C_4$ alkyl, $R^2$ is H or $CH_3$ and $R^3$ and $R^4$ are independently H or $C_1$-$C_4$ alkyl provided that at least one of $R^3$ and $R^4$ is H when $R^2$ is $CH_3$.

U.S. Pat. No. 4,426,392 issued Jan. 17, 1984 to A. C. Goudie discloses antiinflammatory naphthyl compounds of the formula

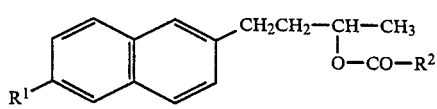

wherein $R^1$ is chloro or methoxy and $R^2$ is methyl, ethyl, benzyl, 2-methoxyethyl, phenyl, 4-methoxyphenyl or aminomethyl.

European patent application No. 0082005 filed Dec. 13, 1982 by Nelson et al., discloses antiinflammatory naphthoxyalkylamines of the formula

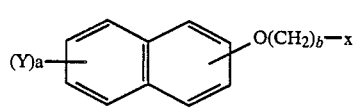

wherein Y is halo, alkoxy, or alkyl; a is 0 or 1; b is an integer from 2-12 with the proviso that if b is 2 or 3, a cannot be O; and x is selected from —OH, $OR^1$, $NH_2$, $NHR^1$, $NR_1^2$,

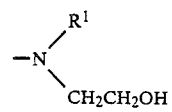

and —NHCONHR² in which each $R^1$ is independently alkyl or phenyl or in —$NR_2^1$, both $R^1$ together are alkylene; and $R^2$ is cycloalkyl or phenyl.

European patent application No. 0036502 filed Feb. 25, 1981 by G. Wurm discloses naphthoquinones of the formula

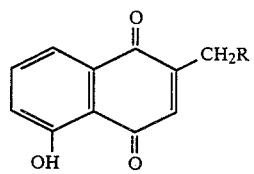

wherein R is methyl, ethyl, propyl, isopropyl, or tertiary butyl. These compounds are disclosed as prostaglandin synthetase inhibitors, useful in the treatment of allergy and anaphylactic shock.

European patent application No. 0127726 filed Jan. 27, 1984 by Slapke et al., discloses aromatic hydroxamic acid derivatives as 5-lipoxygenase inhibitors useful in the treatment of asthma. Included is the compound having the formula

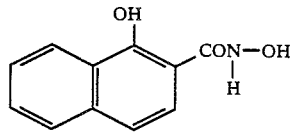

U.K. Pat. No. 2055097 issued Feb. 25, 1981 to Terao et al. discloses quinone derivatives of the formula

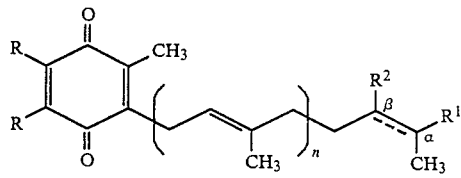

wherein α-β means a saturated bond or double bond; each R independently of one another is a methyl or methoxy group, or two R's taken together represent a —CH=CH—CH=CH— group; n is 0-9; $R^2$ is H or OH when α-β is saturated, $R^2$ is H when α-β is a double bond; when α-β is a double bond or when $R^2$ is OH, $R^1$ is COOH, a —$(CH_2)_m$OH group or

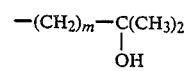

group when α-β is a saturated bond and $R_2$ is H, $R^1$ is hydroxymethyl or

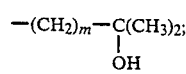

m=1 to 3. These compounds are active as bronchodilators useful in the treatment of asthma.

G. Xi et al. in *Yaoxue Xuebao* 15, 548 (1980) discloses the synthesis of antiasthmatic quinones of the formula

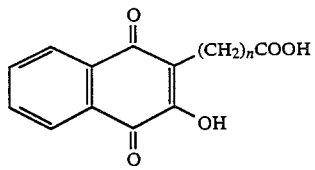

where n=4–8. A number of alkyl naphthols are disclosed as intermediates.

A number of references disclose 1-naphthol as a lipoxygenase inhibitor, including T. Nakadate et al., *Gann*, 75, 214 (1984); J. Van Wauwe and J. Goossens, *Prostaglandins*, 26, 725 (1983); and R. V. Panganamala et al., *Prostaglandins*, 14, 261 (1977).

M. Shiraishi and S. Tereo in *J. Chem. Soc. Perkin Trans. I*, 1591 (1983) disclose ethylenic and acetylenic quinones which inhibit 5-lipoxygenase.

A number of references disclose 2-alkyl-1-naphthols as intermediates in the preparation of other chemical compounds including N. S. Narasimhan and R. S. Mali, *Tetrahedron*, 31, 1005 (1975); Newman et al., *J. Org. Chem*, 43, 524 (1978); B. Miller and W. Lin, *J Org. Chem*, 43, 4441 (1978); K. A. Parker and J. L. Kallmerton, *Tetrahedron Letters*, 14, 1197 (1979); D. W. Cameron et al., *Aust J. Chem*, 35, 1481 (1982); P. Barua et al., *Chem Ind.* 303 (1984); T. Kometani et al., *J. Org. Chem.*, 48, 2630 (1983); T. Zhong and M. Huang, *Hua Hseuh Hseuh Pao*, 39, 229 (1981); C. Pac et al., *Synthesis*, 589 (1978); I. A. Akhtar and J. J. McCullough in *J. Org. Chem.*, 46, 1447 (1981); R. Alonso Cermona et al., *An. Quim.*, Ser. C, 78, 9 (1982); I. M. Andreeva et al., *Khim. Geterotsikl. Soedin.* 2, 181 (1983); D. Berney and K. Schuh, *Helv. Chim. Acta*, 62, 1268 (1979); S. P. Starkov, *Izv. Vyssh. Uchebn. Zaved., Khim. Khim. Tekhnol.* 20, 1099 (1977); M. R. Saidi, *Indian J. Chem.*, 474 (1982); L. Z. Oblasova and G. D. Kharlampovich, *Khim. Pro-St. (Moscow)*, 10, 776 (1977); F. T. Sher and G. A. Berchtold, *J. Org. Chem*, 42, 2569 (1977); M. Mully et al., *Helv. Chim. Acta*, 58, 610 (1975); T. R. Kasturi and R. Sivaramakrishnan, *Proc. Indian Acad. Sci.*, 86, 309 (1977) and T. Hirashima et., in Japanese Pat. No. 7010339 issued Apr. 14, 1970.

A number of references disclose 2-benzyl-1-naphthol as a chemical entity, such as B. Miller and W. Lin, *J. Org. Chem*, 44, 887 (1979) and Z. Aizenshtat et al., *J. Org. Chem*, 42, 2386 (1977).

SUMMARY OF THE INVENTION

According to the present invention there are provided pharmaceutical compositions containing 2-substituted-1-naphthols of Formula (I) and pharmaceutical methods for using them.

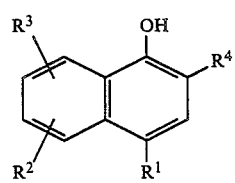

wherein $R^1$ is H, $CH_3$, Br, Cl, OH, $OCH_3$, $OC_2H_5$, $COR^{17}$, $COOR^{18}$, $CONR^{19}R^{20}$, phenyl, $-N(R^{12})(R^{13})$,

lower alkyl, $S(O)_p$ lower alkyl where p is 0, 1 or 2, $SO_2NH_2$, or $-NHSO_2$ lower alkyl optionally substituted with F;

$R^2$ and $R^3$ independently are H, $CH_3$, $C_2H_5$, $OCH_3$, or $OC_2H_5$;

$R^4$ is straight-chain or branched alkyl of 1–12 carbons,
straight-chain or branched alkenyl of 2–12 carbons,
straight-chain or branched alkynyl of 2–12 carbons,
cycloalkyl or cycloalkenyl of 5–7 carbons,
$CH_2-C\equiv C-(CH_2)_m R^5$ where m is 1–4,
$CH=CH-(CH_2)_n R^5$ where n is 0–3 and the olefinic bond has either the Z or E configuration
$A-R^6$, or

A is a chain of 2–6 methylene groups optionally substituted at any one of the methylene carbons by a group $R^8$;

$R^5$ is $C_5-C_7$ cycloalkyl, phenyl, $COOR^9$, $R^6$ is $C_5-C_7$ cycloalkyl, phenyl, $COOR^9$, $CON(R^{12})(R^{13})$, CN, $CH(COOR^9)_2$, $C(R^{10})(R^{11})OR^9$, $P(O)(OR^9)_2$, $S(O)_w R^9$ where w is 0–2 with the proviso that if w=1 then $R^9$ is not H; $SC(NH)NH_2$, $N(R^{12})(R^{13})$, $OR^9$, $(OC(O)R^9$, Cl, Br, or I;

$R^7$ is $C_3-C_8$ cycloakyl

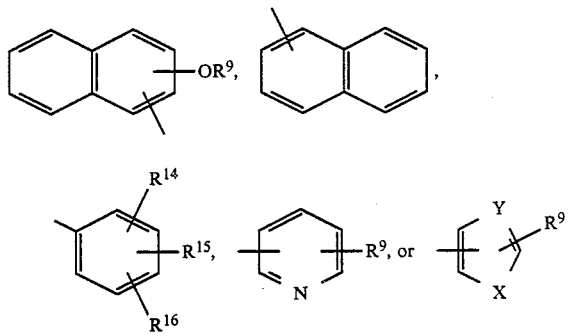

where X is S, O, or $NR^{10}$, and Y is CH or N;
$R^8$ is $C_1-C_4$ alkyl, $C_5-C_7$ cycloalkyl, or phenyl;
$R^9$, $R^{10}$, and $R^{11}$ are independently H or $C_1-C_4$ alkyl;
$R^{12}$ and $R^{13}$ independently are H, $C_1-C_4$ alkyl, or together are $(CH_2)_{4-5}$;
$R^{14}$ is H, $C_1-C_4$ alkyl, $OR^9$, O-phenyl, $OCH_2COOR^9$, O-benzyl, $COOR^9$, $CF_3$, Cl, Br, I, $N(R^{12})(R^{13})$, or $S(O)_w R^9$ where w is 0–2 with the proviso that if w is 1 then $R^9$ is not H;
$R^{15}$ and $R^{16}$ are independently H, $C_1-C_4$ alkyl, $OR^9$, O-benzyl, F, or Cl;
$R^{17}$ is lower alkyl, phenyl, optionally monosubstituted with Cl, Br, F, $CH_3$, $CH_3O$, pyridyl, thienyl or furyl;
$R^{18}$ is H or lower alkyl;

$R^{19}$ and $R^{20}$ independently are H or lower alkyl, or taken together are $(CH_2)_{4-5}$; and $R^{21}$ is H, lower alkyl, phenyl, optionally monosubstituted with Cl, Br, F, $CH_3$, $CH_3O$, pyridyl, thienyl, or furyl;

or a pharmaceutically suitable salt thereof.

Pharmaceutical compositions preferred for their 5-lipoxygenase activity contain a compound of Formula (I) where:

$R^4$ is straight-chain or branched alkyl of 1–6 carbons; allyl optionally substituted on the double bond carbons with methyl or ethyl groups;
cycloalkyl or cycloalkenyl of 5–6 carbons;
$CH_2$—$C\equiv C$—$(CH_2)_m R^5$ where m is 3 and $R^5$ is $COOR^9$ or phenyl;
$CH=CH$—$(CH_2)_n R^5$ where n is 0–2, the olefinic bond has either the Z or E configuration, and $R^5$ is $COOR^9$, or phenyl;
A—$R^6$; or
$CH_2$—$R^7$; where A, $R^6$ and $R^7$ are as defined above, preferably A is a chain of 2–6 unsubstituted methylene groups;
$R^6$ is phenyl, $COOR^9$, $CON(R^{12})(R^{13})$, CN, $CH(COOR^9)_2$, $C(R^{10})(R^{11})OR^9$, $P(O)(OR^9)_2$, $S(O)_w R^9$, $SC(NH)NH_2$, $N(R^{12})(R^{13})$, $OR^9$, $OC$-$(O)R^9$, Cl, Br, or I;
$R^7$ is as defined above except that X is restricted to S, O, or N—$CH_3$;
$R^{14}$ is as defined above except for O-phenyl, O-benzyl, and $OCH_2COOR^9$;
$R^{15}$ and $R^{16}$ are independently H, $OR^9$, F, or Cl; and w, $R^9$, $R^{10}$, $R^{11}$, $R^{12}$ and $R^{13}$ are as defined above.

Specifically preferred for their lipoxygenase inhibitory activity are:

a. methyl 7-(1-hydroxy-2-naphthyl)-5-heptynoate
b. ethyl 5-(1-hydroxy-2-naphthyl)-4-pentenoate, Z isomer
c. ethyl 3-(1-hydroxy-2-naphthyl)-propenoate, E isomer
d. 2-(2-propenyl)-1-naphthol
e. ethyl 3-(1-hydroxy-2-naphthyl)-propanoate
f. ethyl 5-(1-hydroxy-2-naphthyl)-pentanoate
g. 2-(5-methylhexyl)-1-naphthol
h. diethyl [3-(1-hydroxy-2-naphthyl)propyl]propanedioate
i. 2-(phenylmethyl)-1-naphthol
j. 2-(3-fluorophenylmethyl)-1-naphthol
k. 2-[(3,4,5-trimethoxyphenyl)methyl]-1-naphthol
l. 2-(2-furylmethyl)-1-naphthol
m. 2-[(3,4-dimethoxyphenyl)methyl]-1-naphthol
n. 2-(2-thienylmethyl)-1-naphthol
o. 2-(3-chlorophenylmethyl)-1-naphthol
p. 2-(4-ethoxyphenylmethyl)-1-naphthol
q. 2-(4-bromophenylmethyl)-1-naphthol
r. 5,8-dimethyl-2-(phenylmethyl)-1-naphthol Also provided in the invention are novel 2-substituted -1-naphthols within Formula (I) which are defined by Formula (II).

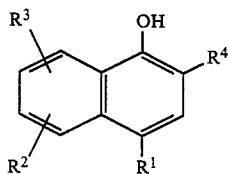
(II)

wherein $R^1$ is H, $CH_3$, Br, Cl, $OC_2H_5$, $COR^{17}$, $COOR^{18}$, $CONR^{19}R^{20}$, phenyl, —$S(O)_p$ lower alkyl, where p is 0, 1 or 2, —$N(R^{12})(R^{13})$,

lower alkyl, $SO_2NH_2$, —$NHSO_2$ lower alkyl optionally substituted with F;
$R^2$ and $R^3$ independently are H, $CH_3$, $C_2H_5$, $CH_3O$, or $C_2H_5O$;
$R^4$ is straight-chain or branched alkynyl of 2–12 carbons,
$C_5$–$C_7$ cycloalkenyl,
$CH_2$—$C\equiv C$—$(CH_2)_m R^5$ where m is 1–4,
$CH=CH$—$(CH_2)_n R^5$ where n is 1–3 and the olefinic bond has either the Z or E configuration,
A—$R^6$, or

A is a chain of 2–6 methylene groups;
$R^5$ is $C_5$-$C_7$ cycloalkyl, phenyl, $COOR^9$;
$R^6$ is $C_3$–$C_6$ alkenyl, $C_5$–$C_7$ cycloalkyl, $CON(R^{12})(R^{13})$, CN, $CH(COOR^9)_2$, $C(R^{10})(R^{11})OR^9$, $P(O)(OR^9)_2$, $S(O)_w R^9$ where w is 0–2 with the proviso that if w is 1 then $R^9$ is not H, $SC(NH)NH_2$, $N(R^{12})(R^{13})$, $OR^9$, Cl, Br, or I;
$R^7$ is $C_3$–$C_8$ cycloalkyl,

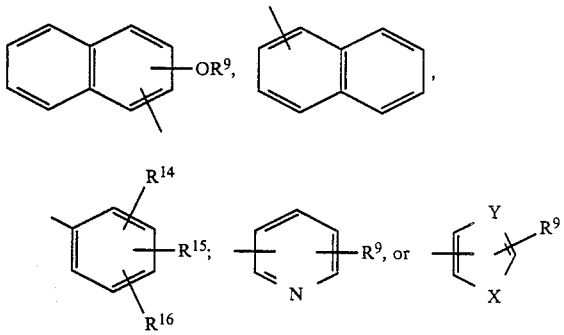

where X is S, O, or $NR^{10}$, and Y is CH or N;
$R^9$, and $R^{10}$, and $R^{11}$ are independently H or $C_1$–$C_4$ alkyl;
$R^{12}$ and $R^{13}$ independently are H, $C_1$–$C_4$ alkyl, or together are $(CH_2)_{4-5}$;
$R^{14}$ is $C_1$–$C_4$ alkyl, $OR^9$, O-phenyl, $OCH_2COOR^9$, O-benzyl, $COOR^9$, $CF_3$, Cl, Br, I, $N(R^{12})(R^{13})$, or $S(O)_w R^9$ where w is 0–2 with the proviso that if w is 1 then $R^9$ is not H; and
$R^{15}$ and $R^{16}$ are independently H, $C_1$–$C_4$ alkyl, $OR^9$, O-benzyl, F or Cl;
$R^{17}$ is lower alkyl, phenyl optionally monosubstituted with Cl, Br, F, $CH_3$, $CH_3O$, pyridyl, thienyl or furyl;
$R^{18}$ is H or lower alkyl;
$R^{19}$ and $R^{20}$ independently are H or lower alkyl, or taken together are $(CH_2)_{4-5}$; and
$R^{21}$ is H, lower alkyl, phenyl optionally monosubstituted with Cl, Br, F, $CH_3$, $CH_3O$, pyridyl, thienyl, or furyl; subject to the following provisos;

1. if $R^1$, $R^2$, and $R^3$ are all H, then $R^4$ is not 4-chlorophenylmethyl, 4-methylphenylmethyl, or 2-furylmethyl;
2. if $R^2$ or $R^3$ is 6—$OCH_3$, then $R^4$ is not 4-chlorophenylmethyl or 4-methylphenylmethyl;
3. if $R^1$ is Cl then $R^4$ is not 4-aminophenylmethyl; and
4. $R^4$ is not $CH_2CH_2CN$.

Preferred for their lipoxygenase activity are those novel compounds of Formula (II) where:

$R^4$ is cycloalkenyl of 5-6 carbons;
$CH_2$—C≡C—$(CH_2)_mR^5$ where m is 3 and $R^5$ is $COOR^9$ or phenyl;
CH=CH—$(CH_2)_nR^5$ where n is 1-2, the olefinic bond has either the Z or E configuration and $R^5$ is $COOR^9$ or phenyl;
A—$R^6$; or
$CH_2$—$R^7$; where A, $R^6$ and $R^7$ are as defined above, preferably
A is a chain of 2-6 unsubstituted methylene groups;
$R^6$ is $CON(R^{12})(R^{13})$, CN, $CH(COOR^9)_2$, $C(R^{10})(R^{11})OR^9$, $P(O)(OR^9)_2$, $S(O)_wR^9$, $SC(NH)NH_2$, $N(R^{12})(R^{13})$, $OR^9$, Cl, Br, or I;
$R^7$ is as defined above except that X is restricted to S, O, or N—$CH_3$;
$R^{14}$ is as defined above except for O-phenyl, O-benzyl, and $OCH_2COOR^9$;
$R^{15}$ and $R^{16}$ are independently H, $OR^9$, F, or Cl; and w, $R^9$, $R^{10}$, $R^{11}$, $R^{12}$ and $R^{13}$ are as defined above.

Specifically preferred novel compounds are the same ones specifically preferred for their lipoxygenase activity except compounds c, d, e, f, g and i.

As used herein, the term "lower alkyl" means a straight chain or a branched-chain alkyl of 1 to 4 carbon atoms.

DETAILED DESCRIPTION OF THE INVENTION

The novel compounds of Formula (II) may be prepared using the reactions and techniques described in this section. The reactions are usually performed in a solvent appropriate to the reagents and materials employed, and suitable for the transformation being effected. Unless stated otherwise, the reactions are performed at temperatures between −78° and the boiling point of the solvent used, as appropriate for a reasonable rate of reaction and the stability of the reagents, solvents, and products involved.

Throughout the following section, the preparation of certain compounds of Formula (II) by the methods described will require that functional groups on the starting materials be protected, by the use of standard protecting groups reported in the chemical literature. These cases will be readily recognized by one skilled in the art. Examples of suitable protecting groups include benzyl ethers, methyl ethers, and methoxymethyl ethers to protect hydroxyl groups, ketals and acetals to protect carbonyl groups, and trialkyl orthoesters to protect esters. The choice of protecting groups is affected by the type of transformations to be performed upon the protected material, as well as the types of functionality elsewhere in the molecule which must be stable to the conditions used to remove the protecting group after it has served its purpose. A review of protecting group chemistry is T. W. Greene, "Protective Groups in Organic Synthesis" (John Wiley and Sons, 1981). In the cases where a protecting group is required, this group must often be removed in a separate step after performing those steps of the synthetic route with which the unprotected functionality is not compatible.

Throughout the following section, not all compounds of Formula (II) falling into a given class may necessarily be prepared by all methods described for that class. Substituents on the starting materials may be incompatible with some of the reaction conditions required in some of the methods described. Such restrictions in the substituents which are compatible with the reaction conditions will be readily apparent to one skilled in the art. Alternative methods described in the following section may then be used to prepare such compounds.

Throughout the following section, the letter "Z" in the Formulas represents the portion of $R^4$ which is not already included in the formula, or the portion of $R^4$ not involved in the manipulations illustrated in the Schemes. The letters "Pr" represent a protecting group for the naphthol hydroxyl which is suitable for the transformations being illustrated, and which may be removed under conditions which will not affect the remainder of the compound. Examples of such protected hydroxyl groups are methyl, benzyl, methoxymethyl, and trialkylsilyl ethers. The choice of a suitable protecting group will be apparent to one skilled in the art.

Compounds of Formula (II) where $R^4$ is an alkynyl group attached to the naphthalene ring through a methylene group may be prepared by the route shown in Scheme 1. A suitable 1-(protected hydroxy)-2-naphthaldehyde (III) may be treated with an alkynyl organometallic reagent such as an organolithium reagent to provide the intermediate alcohol (IV). This intermediate compound may be converted to the intermediate protected naphthol (V) using standard methods of hydroxyl group removal, for instance by treatment with a trialkylsilane in the presence of an acid reagent such as boron trifluoride etherate. An example of this reductive dehydroxylation method is described by J. L. Fry et al., *Tetrahedron Letters*, 2995 (1976). The protecting group of (V) may then be removed using appropriate techniques to provide the desired (II).

SCHEME 1:

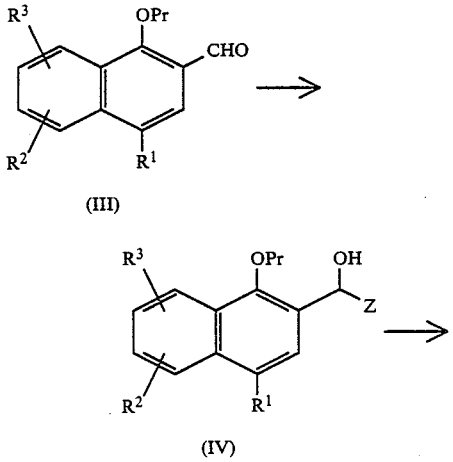

-continued
SCHEME 1:

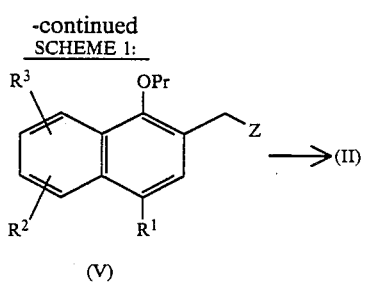

(V)

Compounds of Formula (II) where $R^4$ is an alkynyl group attached to the naphthalene ring through one of the acetylenic carbons may be prepared as shown in Scheme 2. A suitable 1-(protected hydroxyl)-2-bromonaphthalene (VI) may be treated with a 1-alkyne in the presence of a suitable catalyst such as a palladium salt, for instance as reported by W. B. Austin et al., *J. Org. Chem.* 46, 2280 (1981), to provide the intermediate protected alkynyl naphthol (VII). Alternatively, a suitable 1-(protected hydroxy)-2-naphthaldehyde (III) may be treated with tetrabromomethane and triphenylphosphine to provide the intermediate acetylenic compound (VIII). This intermediate may then be treated with a strong base such as n-butyllithium and an electrophilic reagent such as an alkyl halide to provide the intermediate (VII). (This method of forming substituted acetylenes is reported by E. J. Corey and P. L. Fuchs, *Tetrahedron Letters*, 3769 (1972).) The protecting group of (VII) may then be removed using appropriate techniques to provide the desired (II).

Compounds of Formula (II) where $R^4$ is $CH_2$—C≡C—$(CH_2)_m R^5$ may be prepared by the route shown in Scheme 1.

converted to the intermediate cycloolefin (XII) by dehydration using standard methods such as treatment with an acid, e.g., hydrochloric acid or p-toluenesulfonic acid. The protecting group of (XII) may then be removed using appropriate techniques to provide the desired (II).

SCHEME 3:

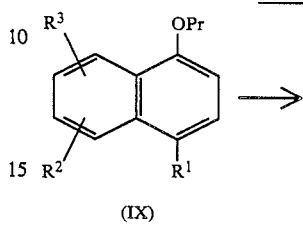

(IX)

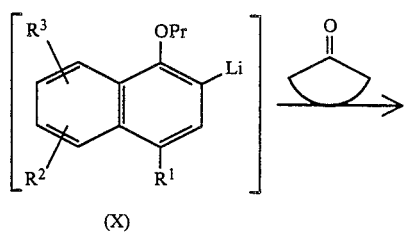

(X)

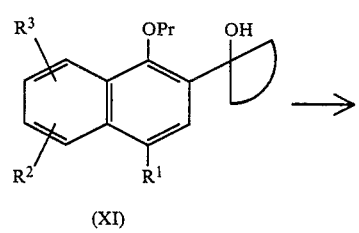

(XI)

SCHEME 2:

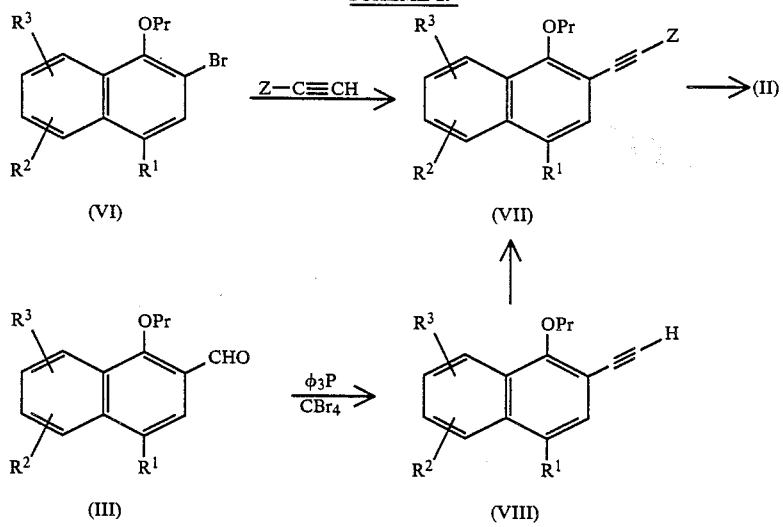

Compounds of Formula (II) where $R^4$ is a cycloalkenyl group may be prepared as shown in Scheme 3. A suitable protected 1-naphthol (IX) may be treated with a strong base such as n-butyllithium to provide the organolithium intermediate (X). An example of this transformation is reported by D. A. Shirley and C. F. Cheng, *J. Organometallic Chem.* 20, 251 (1969). The organolithium derivative (X) may then be treated with a suitable ketone, such as cyclopentanone, cyclohexanone, or cycloheptanone, to provide the intermediate tertiary alcohol (XI). The intermediate (XI) may be -continued
SCHEME 3:

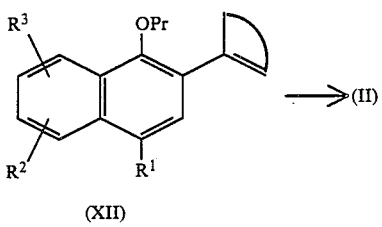

(XII)

Compounds of Formula (II) where $R^4$ is $CH=CH—(CH_2)_nR^5$ may be prepared by the route shown in Scheme 4. A suitable 1-(protected hydroxy)-2-naphthaldehyde (III) may be treated with a reagent such as an alkylidene triarylphosphorane (XIII) or the anion of a dialkyl alkylphosphonate (XIV) (the Wittig reaction) to provide the protected intermediate (XV), which may be obtained as either the Z or the E isomer, or as a mixture of the two. The protecting group may be removed using appropriate techniques to provide the desired (II).

Compounds of formula (II) where $R^4$ is $CH=CH—(CH_2)_nR^5$ may also be prepared by an alternative route also shown in Scheme 4. An organolithium derivative (X), prepared from a suitable protected 1-naphthol (IX), may be treated with an aldehyde $ZCH_2CHO$. The intermediate alcohol (XVI) may then be dehydrated using standard methods such as treatment with an acid, e.g., hydrochloric acid or p-toluenesulfonic acid. The resulting intermediate (XV) may then be deprotected using appropriate techniques to provide the desired (II).

Guo, and R. Chen, *Yaoxue Xuebao* 15, 548 (1980), and by G. Faway and L. F. Fieser, *J. Amer. Chem. Soc.* 72, 996 (1950). The intermediate ketone (XVIII) may be converted to the desired (II) by standard methods, for instance by treatment with amalgamated zinc in the presence of hydrochloric acid (the Clemmensen reduction technique), or by conversion of the naphthol hydroxyl group to an ethyl carbonate followed by treatment with sodium borohydride, a technique reported by V. G. Wurm et al., *Arzneimittel-Forschung* 34, 652 (1984).

SCHEME 5:

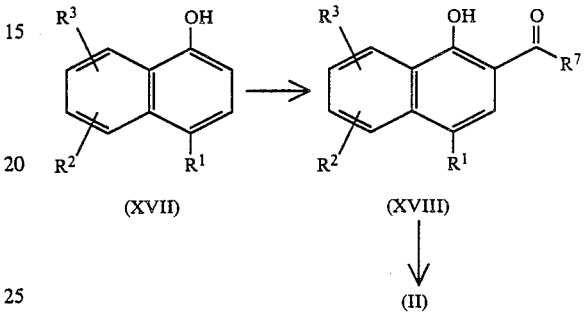

Compounds of Formula (II) where $R^4$ is $CH_2—R^7$, where $R^7$ is an aromatic group, may also be prepared by the method shown in Scheme 6. A suitable 1-tetralone (XIX) may be treated with an aryl or heteroaryl aldehyde in the presence of a base such as potassium hydroxide or potassium t-butoxide in an alcoholic solvent. If the base/solvent combination is potassium t-butoxide and t-butanol, the 2-arylmethyl-1-naphthol ((II) where

SCHEME 4:

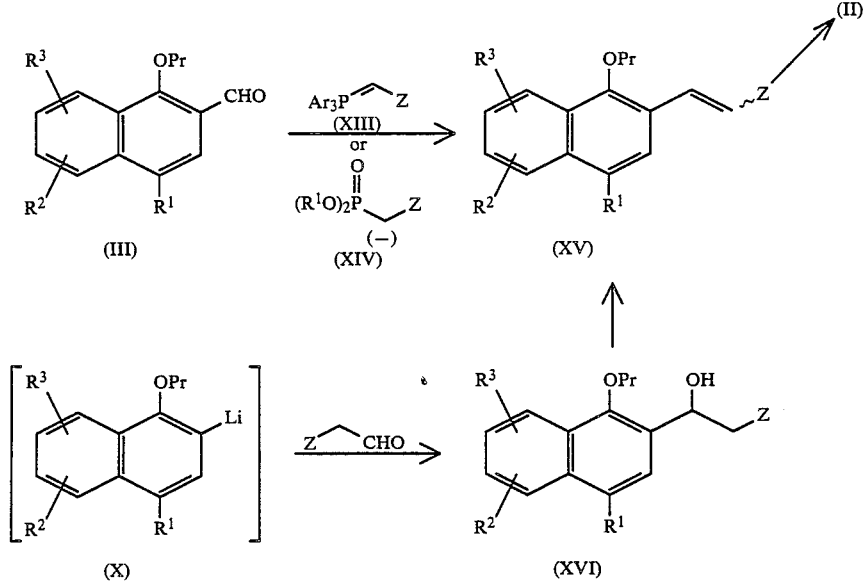

Compounds of Formula (II) where $R^4$ is $CH_2—R^7$ may be prepared by the method illustrated in Scheme 1.

Compounds of Formula (II) where $R^4$ is $CH_2—R^7$ may also be prepared by the method illustrated in Scheme 5. A suitable naphthol (XVII) may be treated with a suitable carboxylic acid derivative, such as the free acid, acid halide, or anhydride, in the presence of a suitable acid catalyst (the Friedel-Crafts reaction). Examples of this type of reaction are reported by G. Xi, X.

$R^4$ is $CH_2—R^7$) is obtained after workup with aqueous acid. If the base/solvent combination is potassium hydroxide and ethanol, an intermediate benzylidene tetralone (XX) is isolated, as reported by Z. Aizenshtat, M. Hausmann, Y. Pickholtz, D. Tal, and J. Blum, *J. Org. Chem.* 42, 2386 (1977). This intermediate may then be treated with potassium t-butoxide in t-butanol to provide (II) where $R^4$ is $CH_2R^7$ after workup with aqueous acid, as reported by D. H. R. Barton, J. H. Bateson, S. C. Datta, and P. D. Magnus, *J. Chem. Soc., Perkin Trans. I*, 503 (1976).

SCHEME 6:

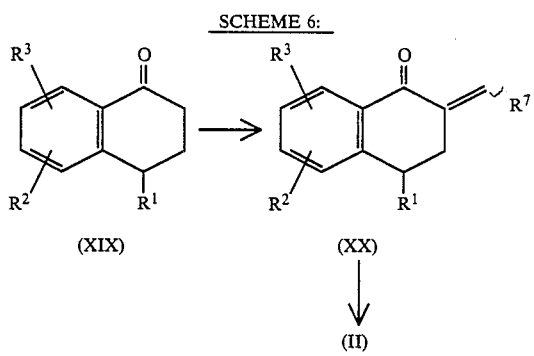

(XIX) (XX)

↓

(II)

Compounds of Formula (II) where $R^4$ is $CH(R^{21})R^7$ may be prepared by the methods shown in Scheme 7. An organolithium derivative (X), prepared from a suitable protected 1-naphthol (IX), may be treated with a ketone to provide the tertiary alcohol (XXI) after aqueous workup. Alternatively, a ketone (XXII) prepared by protection of the hydroxyl group of a ketone (XVIII), where Z is either $R^7$ or $R^{21}$, may be treated with an organometallic reagent Z'M, where Z' is $R^7$ (if Z is $R^{21}$) or $R^{21}$ (if Z is $R^7$), and M is a metal such as lithium or magnesium halide. The intermediate (XXI) resulting from either of these reactions may be converted to the intermediate (XXIII) using standard methods of reductive dehydroxylation. Removal of the protecting group from (XXIII) will then provide the desired (II).

Compounds of Formula (II) where $R^4$ is $A-R^6$ may be prepared by the routes shown in Schemes 1 or 5.

Compounds of Formula (II) where $R^4$ is $A-R^6$ may also be prepared from certain compounds of Formula (II) having an olefinic group for $R^4$ (which may be prepared according to the routes shown in Scheme 4). Reduction of the multiple bond may be performed using standard methods, for instance treatment with hydrogen in the presence of a catalyst such as palladium on charcoal.

Compounds of Formula (II) where $R^4$ is $A-R^6$ may also be prepared by the route shown in Scheme 8. An organolithium derivative (X), prepared from a suitable protected 1-naphthol (IX), may be treated with an alkylating agent such as an alkyl halide to provide the intermediate (XXIV). The resulting intermediate may then be deprotected using appropriate techniques to provide the desired (II).

SCHEME 8

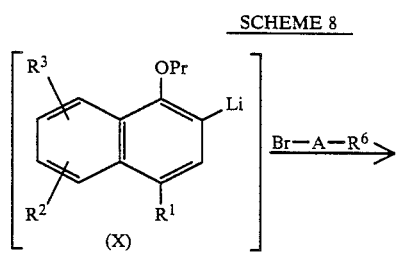

SCHEME 7:

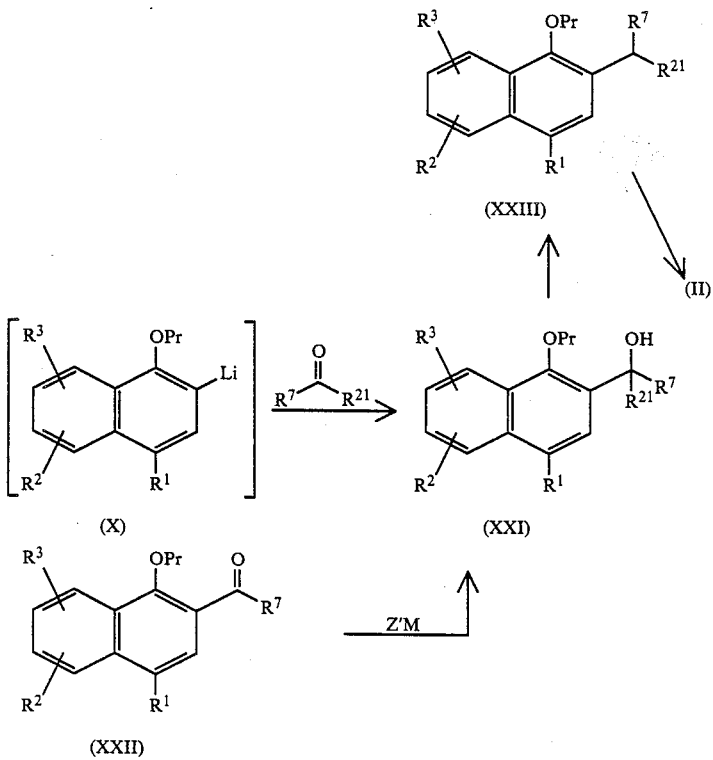

-continued
SCHEME 8

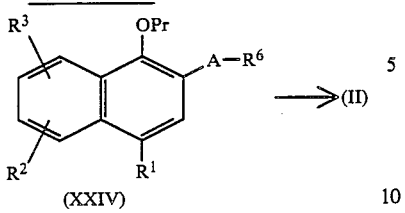

(XXIV) → (II)

Compounds of Formula (II) where $R^4$ is $(CH_2)_3$—OH may be prepared by the route shown in Scheme 9. The allyl ether of a suitable 1-naphthol (XXV) may be converted to the 2-allyl-1-naphthol (XXVI) by thermal rearrangement, for instance as described by K. A. Parker and J. L. Kallmerten, *Tetrahedron Letters*, 1197 (1979). The intermediate (XXVI) may then be converted to a protected form (XXVII), and converted to the protected hydroxyl compound (XXVIII) by treatment with borane-tetrahydrofuran complex followed by a standard oxidative workup. Deprotection of (XXVIII) will then provide the desired (II).

Compounds of Formula (II) where $R^4$ is $(CH_2)_nOH$, where n is 2–6, may also be prepared from the corresponding compounds of Formula (II) where $R^4$ is $(CH_2)_{n-1}R^6$, where $R^6$ is a carboxylic acid, carboxylic ester, or aldehyde, by treatment with a reducing agent such as lithium aluminum hydride.

SCHEME 9

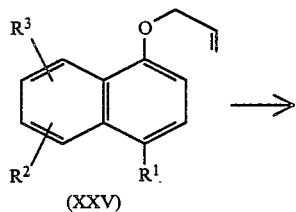

(XXV)

-continued
SCHEME 9

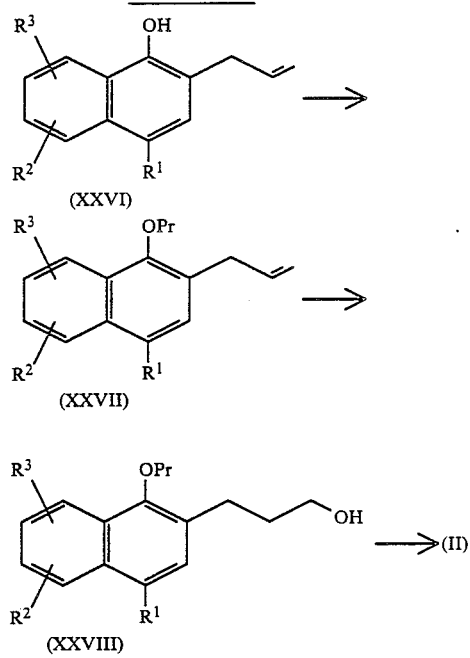

Compounds of Formula (II) may also be prepared from other compounds of Formula (II) by functional group interconversions which are well known to those skilled in the art. Examples of such functional group interconversions are given herein.

Compounds of Formula (II) where $R^4$ contains the group $C(R^{10})(R^{11})OH$ may be prepared from the corresponding compounds where this group is replaced by a carboxylic ester or carboxylic acid, as shown in Scheme 10. The ester or acid (XXIX) may be treated with an appropriate organometallic reagent such as an alkyllithium or alkylmagnesium halide to provide the desired compound (XXX), where $R^{10}$ and $R^{11}$ are the same. If $R^{10}$ and $R^{11}$ are different, the corresponding compound (XXX) may be prepared by treating the ester or carboxylic acid (XXIX) with an appropriate organometallic reagent to provide the intermediate alkyl ketone (XXXI). Treatment of this intermediate with either a reducing agent such as sodium borohydride or with a second organometallic reagent will then provide the desired compound (XXX).

SCHEME 10

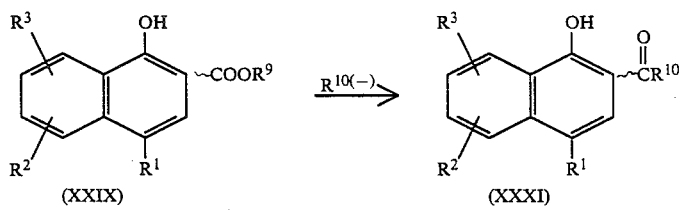

SCHEME 10

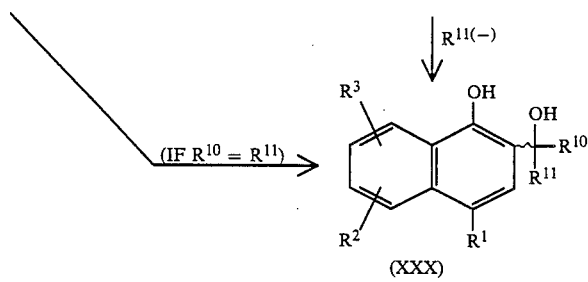

(XXX)

Compounds of Formula (II) where R⁴ contains a C₃–C₆ alkylene group may be prepared from compounds of Formula (XXX) by dehydration using standard techniques.

Compounds of Formula (II) where R⁴ contains an aliphatic halogen atom may be prepared from the corresponding alcohol using standard procedures. Compounds of this type may also be converted into compounds with a different halogen using standard procedures.

Compounds of Formula (II) where R⁴ contains an aliphatic nitrile, malonic ester, phosphonic ester, sulfide, amine, ether, or SC(NH)NH₂ group may be prepared from the corresponding compound containing a suitable leaving group such as Cl, Br, I, methanesulfonate, toluenesulfonate, or trifluoromethanesulfonate by treatment with an appropriate nucleophilic reagent such as sodium cyanide, diethyl sodiomalonate, triethyl phosphite, potassium thiomethylate, sodium ethoxide, thiourea, etc. (Sulfonate leaving groups may be prepared by treatment of the corresponding alcohol with the appropriate sulfonyl chloride or sulfonic anhydride in the presence of a base such as triethylamine or pyridine.) In the case where R⁴ contains SH, thiourea may be used as the nucleophile, in which case basic hydrolysis of the intermediate isothiourea provides the thiol. In the case where R⁴ contains NH₂, sodium azide may be used as the nucleophile, in which case catalytic hydrogenation of the intermediate azide provides the primary amine.

Compounds of Formula (II) where R⁴ contains an ether or sulfide group may be prepared by treatment of the corresponding alcohol or thiol (in which the naphthol hydroxyl has been suitably protected) with a strong base such as sodium hydride, followed by treatment with an appropriate alkylating agent such as methyl iodide or ethyl iodide, and removal of the protecting group.

Compounds of Formula (II) where R⁴ contains a carboxylic ester may be prepared from the corresponding compound where R⁴ contains a halogen such as Br or Cl and the naphthol has been suitably protected, by conversion to the corresponding organolithium or organomagnesium halide and allowing this intermediate to react with a dialkyl carbonate to provide the corresponding ester, followed by deprotection. The corresponding carboxylic acid may be prepared by allowing the organometallic intermediate to react with carbon dioxide, followed by deprotection.

Compounds of Formula (II) where R¹ is Cl or Br may be prepared from the corresponding compound (II) where R¹ is H, by treatment with chlorine or bromine in a suitable solvent such as acetic acid, optionally in the presence of a suitable catalyst. In some cases, it may be preferable to mask the naphthol hydroxyl group prior to reaction with bromine or chlorine, in which case deprotection is required to provide the desired product (II).

Compounds of Formula (II) where R¹ is C(=O)R¹⁷ may be prepared from compounds of Formula (II) where R¹ is hydrogen by treatment with a suitable acylating reagent such as an acid chloride, acid anhydride, or mixed anhydride, in the presence of a catalyst such as aluminum chloride or zinc chloride (the Friedel-Crafts reaction). In some cases, it may be preferable to mask the naphthol hydroxyl group prior to reaction with the acylating reagent, in which case deprotection is required to provide the desired (II). In some cases, the hydroxyl group will react with the acylating agent in the course of the acylation reaction to provide the corresponding ester of the desired (II), in which case hydrolysis of the ester provides the desired (II).

Compounds of Formula (II) where R¹ is C(=O)R¹⁷ may also be prepared from compounds of Formula (II) where R¹ is hydrogen by the route shown in Scheme 11. The hydroxyl group of (II) may be protected to provide (XXXIII). The intermediate (XXXIII) may then be treated with bromine in a suitable solvent such as acetic acid to provide (XXXIV). This intermediate may then be converted to an organometallic intermediate (XXXV) such as the corresponding organomagnesium halide or the corresponding organolithium reagent using standard chemical techniques. The organometallic intermediate may then be treated with with a suitable aldehyde R¹⁷—CHO to provide (XXXVI), which may then be oxidized to the corresponding ketone (XXXVII), using reagents such as pyridinium chlorochromate, Jones reagent, or other standard oxidizing agents. Removal of the protecting group on the hydroxyl group using suitable techniques then provides the desired (II).

SCHEME 11

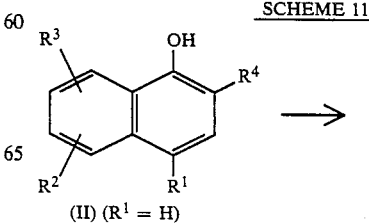

(II) (R¹ = H)

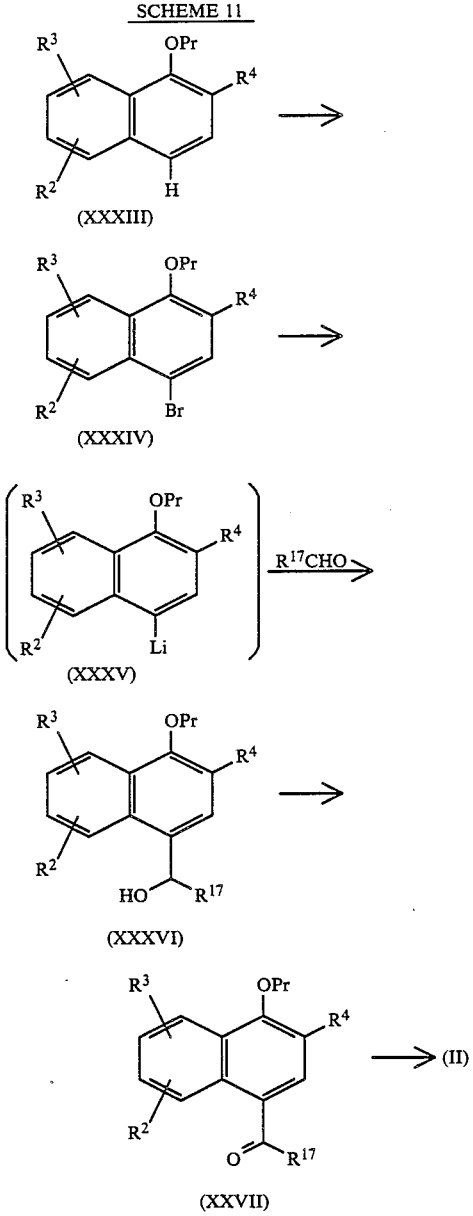

Compounds of formula (II) where $R^1$ is $COOR^{18}$ may be prepared from organometallic intermediates of Formula (XXXV) with a carboxylating agent such as carbon dioxide, a dialkyl carbonate, or an alkyl chloroformate. Removal of the protecting group on the hydroxyl using suitable techniques then provides the desired (II).

Compounds of Formula (II) where $R^1$ is phenyl may be prepared by treatment of intermediates of Formula (XXXIV) with an appropriate arylmagnesium halide, in the presence of a suitable transition metal catalyst such as 1,3-bis-(diphenylphosphino)propane nickel (II) chloride, followed by removal of the protecting group on the hydroxyl using suitable techniques.

Compounds of Formula (II) wherein $R^1$ is $S(O)_xR$ or $SO_2NH_2$ may be prepared by treatment of compounds of Formula (XXXIII) with chlorosulfonic acid to provide the corresponding sulfonyl chloride, followed by standard functional group manipulations, well known to one skilled in the art, to convert the sulfonyl chloride to the desired group $S(O)_xR$ or $SO_2NH_2$. Removal of the hydroxyl protecting group will then provide the desired (II).

Compounds of Formula (II) wherein $R^1$ is $NR^{12}R^{13}$ may be prepared from compounds of Formula (XXXIII) by reaction with a suitable nitrating agent in a suitable solvent, such as fuming nitric acid in acetic acid. The intermediate nitro derivative may then be converted to the compound of Formula (II) wherein $R^1$ is $NH_2$ by standard techniques of nitro group reduction, such as catalytic hydrogenation. Standard functional group manipulations well known to one skilled in the art can then be used to convert the primary amine to other desired substituents $NR^{12}R^{13}$, $NHC(=O)$alkyl, or $NHSO_2$ alkyl.

Compounds of Formula (II) containing ester functional groups may be converted to the corresponding compounds containing carboxylic acid groups by acidic or basic hydrolysis using standard conditions. Carboxylic acids may be converted to esters, and esters may be converted to esters of different alcohols, using standard techniques, for instance, by treatment with a catalytic amount of a strong acid such as sulfuric acid in the appropriate alcohol as solvent, optionally with an inert cosolvent to improve solubility of the starting material.

Compounds of Formula (II) containing an amide functional group attached through the carbonyl carbon may be prepared from the corresponding compounds containing a carboxylic acid functional group by protecting the naphthol hydroxyl group, converting the carboxylic acid to an acid chloride using standard techniques, and allowing the acid chloride to react with ammonia or an appropriate amine. Deprotection of the hydroxyl group then provides the desired (II).

Compounds of Formula (II) containing sulfoxide or sulfone functional groups may be prepared from the corresponding sulfides by protecting the naphthol hydroxyl group and treating with an oxidizing agent such as m-chloroperoxybenzoic acid or any of a number of other oxidants, followed by removal of the protecting group.

Starting materials for the synthetic routes described above, such as 1-naphthols, protected 1-naphthols, and 1-tetralones, are either commercially available, are described in the chemical literature, or may be prepared from known compounds by routes described in the chemical literature.

In particular, protected 2-formyl-1-naphthols of Formula (III) may be prepared from a suitably protected 1-naphthol (IX) by treatment with a strong base such as n-butyllithium, followed by treatment with a formylating agent such as N,N-dimethylformamide, as described by N. S. Narasimhan, R. S. Mali, and M. V. Barve, *Synthesis*, 906 (1979). Alternatively, a 1-hydroxy 2-naphthoic acid may be converted to the naphthyl ether—carboxylic ester using standard techniques, and the ester moiety converted to an aldehyde group, again using standard techniques.

The compounds of this invention and their preparation are illustrated further in the following Examples. All temperatures are in degrees Centigrade and parts and percentages by volume. In these Examples, unless otherwise indicated; the reactions were performed under an atmosphere of dry nitrogen; "isolation by extraction" refers to the liquid-liquid extraction of a water-containing mixture with an indicated solvent, followed by drying the organic phase over magnesium sulfate, filtering, and evaporation of the solvent under reduced pressure; chromatography refers to the method of medium-pressure column chromatography described by W. C. Still, M. Kahn, and A. Mitra, *J. Org. Chem.* 43, 2923 (1978).

EXAMPLE 1

PART A

Methyl 7-(1-benzyloxy-2-naphthyl)-7-hydroxy-5-heptynoate

A solution of 1,1,1-trimethoxy-5-hexyne (3.90 g, 0.023 mole) in dry tetrahydrofuran (50 mL) was stirred at −78° and treated with n-butyllithium (1.6M in hexane; 15 mL, 0.024 mole). The solution was stirred for 30 minutes, then treated with a solution of 1-benzyloxy-2-naphthaldehyde (4.25 g, 0.016 mole) in dry tetrahydrofuran (12 mL). The reaction mixture was allowed to warm to room temperature, stirred for 4 hours, and poured into water. The crude product was isolated by extraction with ether and chromatographed with 3:1 ether/hexane. This afforded the title compound (6.15 g, 97%) as an oil.

PART B

Methyl 7-(1-benzyloxy-2-naphthyl)-5-heptynoate

To a solution of boron trifluoride etherate (5.0 mL, 0.041 mole) in methylene chloride (150 mL) at 0°, triethylsilane (20 mL, 0.126 mole) was added, followed by a solution of methyl 7-(1-benzyloxy-2-naphthyl)-7-hydroxy-5-heptynoate (5.00 g, 0.013 mole) in methylene chloride (20 mL). The mixture was stirred for 30 minutes, then poured into saturated aqueous potassium carbonate. The crude product was isolated by extraction with ether, and chromatographed with 1:1 ether/hexane. This provided the title compound (2.42 g, 50%) as an oil.

PART C

Methyl 7-(1-hydroxy-2-naphthyl)-5-heptynoate

A solution of ethanethiol (12.0 mL, 0.162 mole) and boron trifluoride etherate (6.0 mL, 0.049 mole) was stirred at room temperature. A solution of methyl 7-(1-benzyloxy-2-naphthyl)-5-heptynoate (2.05 g, 0.006 mole) in methylene chloride (8 mL) was added, and the mixture was stirred for 1.5 hours, then poured into water. The crude product was isolated by extraction with ether, and chromatographed with 2:1 ether/hexane. The title compound (1.09 g, 71%) was obtained as a colorless oil. Mass spectrum: m/z=282.

The compounds of Example 1, as well as other compounds which can be prepared by the procedure of Example 1, are shown in Table 1.

TABLE 1

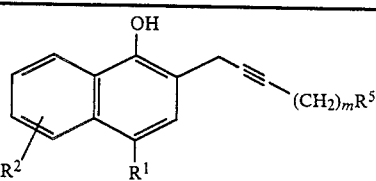

| Ex. | m | R¹ | R² | R⁵ | Yield % | MP(°C.) |
|---|---|---|---|---|---|---|
| 1 | 3 | H | H | COOCH₃ | 71 | (oil)ᵃ |
| 2 | 2 | H | 6-C₂H₅O | C₆H₅ | | |
| 3 | 3 | C₂H₅O | H | cyclohexyl | | |

TABLE 1-continued

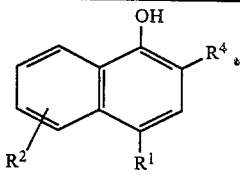

| Ex. | m | R¹ | R² | R⁵ | Yield % | MP(°C.) |
|---|---|---|---|---|---|---|
| 4 | 2 | H | 6-CH₃O | CH(CH₃)₂ | | |

ᵃmass spec m/z = 282

EXAMPLE 5

PART A 2-(1-Hydroxycyclohexyl)-1-methoxymethoxy-naphthalene

A solution of 1-methoxymethoxy-naphthalene (3.76 g, 0.020 mole) in dry ether (40 mL) was treated with n-butyllithium (1.6M in hexane; 25.0 mL, 0.040 mole) at room temperature over a period of 15 minutes. After stirring for an additional 1.5 hours, a solution of cyclohexanone (4.90 g, 0.050 mole) in ether (15 mL) was added and the resulting mixture was stirred at room temperature for 2 hours. It was then quenched with saturated aqueous ammonium chloride and the crude product was isolated by extraction with ether. Chromatography with 9:1 hexane/ethyl acetate provided the title compound as a colorless oil (3.30 g, 58%).

PART B

2-Cyclohexenyl-1-naphthol

A solution of the product of Part A (3.30 g, 0.012 mole) in ethanol (100 mL) and 1.0N hydrochloric acid (100 mL) was stirred at room temperature for 5 hours. The ethanol was removed under reduced pressure, and the crude product was isolated by extraction with ethyl acetate. Chromatography with 95:5 hexane/ethyl acetate provided a white solid which was recrystallized (hexane) to give the title compound (1.59 g, 62%) as white crystals, mp 82°–83°.

The compound of Example 5, as well as other compounds which can be prepared by the procedure of Example 5, are shown in Table 2.

TABLE 2

| Example | R¹ | R² | R⁴ | Yield % | MP(°C.) |
|---|---|---|---|---|---|
| 5 | H | H | cyclohexyl | 62 | 82–83 |
| 6 | H | 6-CH₃O | cyclopentenyl | | |
| 7 | N(CH₂)₄ | H | cycloheptenyl | | |

EXAMPLE 8

Ethyl 4-(1-hydroxy-2-naphthyl)-3-butenoate, E isomer

A suspension of sodium hydride (60% in mineral oil; 1.94 g, 0.049 mole) in dry tetrahydrofuran (20 mL) was stirred at 0°. A solution of 1-methoxymethoxy-2-naphthaldehyde (2.00 g, 0.009 mole) and 2-carboxyethyl-triphenylphosphonium bromide (prepared by the procedure of H. S. Corey, J. R. D. McCormick, and W. E. Swensen, J. Am. Chem. Soc. 86, 1884 (1964); 9.60 g, 0.023 mole) in dry dimethyl sulfoxide (15 mL) was added over 20 minutes. The mixture was allowed to warm to room temperature over 1.25 hours, then stirred at room temperature for 30 minutes. 1.0N hydrochloric acid (10 mL) was added dropwise, followed by stirring for an additional 20 minutes. The crude material was isolated by extraction with ethyl acetate and dissolved in absolute ethanol (200 mL), treated with 10 drops of concentrated sulfuric acid, and heated at reflux for 6 hours. The cooled solution was diluted with water, and the crude product isolated by extraction with ethyl acetate. The resulting oil was chromatographed with 9:1 petroleum ether/ether, to provide a solid which was recrystallized (hexane) to give the title compound (0.35 g, 15%) as a tan solid, mp 83°–84°.

EXAMPLES 9 AND 10

Ethyl 5-(1-hydroxy-2-naphthyl)-4-pentenoate, E and Z isomer

A mixture of potassium t-butoxide (2.10 g, 0.019 mole) and 4-carbethoxypropyl-triphenylphosphonium bromide (prepared according to the procedure of P. E. Sonnet, *J. Org. Chem.* 34, 1147 (1964); 8.40 g, 0.018 mole) in dry tetrahydrofuran (15 mL) was stirred at 0°. After 45 minutes, a solution of 1-methoxymethoxy-2-naphthaldehyde (2.00 g, 0.009 mole) in dry tetrahydrofuran (7.5 mL) was added over 10 minutes. The resulting mixture was stirred at 0° for 2 hours, then was poured into water. The crude material was isolated by extraction with ethyl acetate and chromatographed with 10% ether/petroleum ether, then was dissolved in absolute ethanol (200 mL), treated with 3 drops of sulfuric acid, and heated at reflux for 18 hours. After cooling, the solution was diluted with water and the crude product mixture isolated by extraction with ethyl acetate. This was chromatographed with 85:15 petroleum ether/ether to provide two different solids. The first one to elute was recrystallized (hexane) to provide the Z isomer of the title compound (0.43 g, 17%) as a pale yellow solid, mp 75°–77°. The second solid was recrystallized (hexane) to provide the E isomer (0.23 g, 9%) as a white solid, mp 63°–64°.

The compounds of Examples 8–10, along with other compounds which can be prepared using the procedures of Examples 8–10, are shown in Table 3.

TABLE 3

OH
(structure with naphthalene bearing OH, $R^2$, $R^1$ and vinyl-$(CH_2)_nR^5$ substituent)

| Ex. | $R^1$ | $R^2$ | $R^5$ | n | Z/E | Yield % | MP(°C.) |
|---|---|---|---|---|---|---|---|
| 8 | H | H | $COOC_2H_5$ | 1 | E | 15 | 83–84 |
| 9 | H | H | $COOC_2H_5$ | 2 | E | 9 | 63–64 |
| 10 | H | H | $COOC_2H_5$ | 2 | Z | 17 | 75–77 |
| 11 | $CH_3$ | H | cyclohexyl | 2 | Z | | |
| 12 | $N(CH_3)_2$ | H | phenyl | 2 | Z | | |

EXAMPLE 13

PART A 2-(1',1'-Diphenyl-1'-hydroxy)methyl-1-methoxynaphthalene

A mixture of 1-methoxynaphthalene (7.9 g, 0.05 mole) and cyclohexane (20 mL) was added to a solution of n-butyllithium (1.6M in hexane; 31 mL 0.05 mole) and $N,N,N^1,N^1$-tetramethylethylenediamine (5.8 g, 0.05 mole) in cyclohexane (10 mL). The solution was stirred at room temperature for 2 hours, when a solution of benzophenone (9.1 g, 0.05 mole) in cyclohexane (10 mL) was added. The resulting mixture was stirred overnight and poured into water. The crude product was isolated by extraction with ether, and chromatographed with 19:1 hexane/ethyl acetate. The resulting product was triturated with petroleum ether to provide the title compound (6.13 g, 36%) as a white powder, mp 123°–124.5°.

PART B 2-(1',1'-Diphenylmethyl)-1-methoxynaphthalene

A mixture of boron trifluoride etherate (8.08 g, 0.057 mole) and methylene chloride (150 mL) was stirred at 0°. Triethylsilane (14.56 g, 0.125 mole) was added, followed by a solution of the product of Part A (4.50 g, 0.013 mole) in methylene chloride (20 mL). The mixture was stirred at 0° for 30 minutes and poured into saturated aqueous potassium carbonate. The crude product was isolated by extraction with ether, and triturated with petroleum ether to provide the title compound (4.20 g, 100%) as a white powder, mp 119°–121°.

PART C 2-(1',1'-Diphenylmethyl)-1-naphthol

A mixture of boron tribromide (1.0M in methylene chloride; 10 mL, 10 mmole) in methylene chloride (75 mL) was stirred at −78°. A solution of the product of Part B (2.5 g, 7.7 mmole) was added, and the mixture stirred for 1 hour at −78°. The reaction was then warmed to room temperature, stirred for 5 hours, and poured carefully into water. The crude product was isolated by extraction with ether, and chromatographed with 19:1 hexane/ethyl acetate. The resulting solid was triturated with petroleum ether to provide the title compound (1.06 g, 44%) as a white powder, mp 87°–89°.

EXAMPLE 14

PART A 2-(1'-Cyclohexyl-1'-hydroxy)-methyl-1-methoxynaphthalene

A solution of cyclohexylmagnesium chloride (2.0M in ether; 10 mL, 0.02 mole) in dry ether (10 mL) was stirred at 0°. A solution of 1-methoxy-2-naphthaldehyde (1.88 g, 0.01 mole) in dry ether (15 mL) was added dropwise, and the mixture allowed to warm to room temperature. After stirring for 1 hour, the mixture was poured into 1.0N hydrochloric acid (100 mL). The crude product was isolated by ether extraction and chromatographed with 19:1 toluene-ethyl acetate to provide the title product (1.7 g, 65%) as a pale yellow glass.

PART B

2-Cyclohexylmethyl-1-methoxynaphthalene

Using the procedure of Example 13, Part B, the product of Part A was converted in 77% yield to the title compound, a pale yellow oil. Mass spectrum: m/z 254.

PART C

2-Cyclohexylmethyl-1-naphthol

Using the procedure of Example 13, Part C, the product of Part B was converted in 15% yield to the title compound, a pale orange solid, mp 53°–56°.

The compounds of Examples 13 and 14, along with other compounds which were or can be prepared using the procedure of one of these Examples are shown in Table 4.

acid; and the pH of the resulting mixture was adjusted to 7.0 with 10% aqueous sodium hydroxide.

After isolation by extraction with ethyl acetate, the crude product was recrystallized (benzene) to provide the title compound (4.86 g, 52%) as a tan solid, mp 170°–3°.

EXAMPLE 27

2-(2-Hydroxyphenylmethyl)-1-naphthol

A solution of 1-tetralone (5.85 g, 0.040 mole) and salicylaldehyde (4.88 g, 0.040 mole) in t-butanol (400 mL) was treated with potassium t-butoxide (17.6 g, 0.160 mole) was heated at reflux for 16 hours. After cooling to room temperature, the solution was poured into stirred 1.0N hydrochloric acid. After isolation by extraction with ethyl acetate, the crude product was

TABLE 4

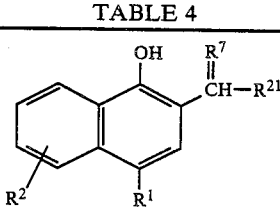

| Ex. No. | $R^1$ | $R^2$ | $R^7$ | $R^{21}$ | YIELD % | MP(°C.) |
|---|---|---|---|---|---|---|
| 13 | H | H | $C_6H_5$ | $C_6H_5$ | 44 | 87–89 |
| 14 | H | H | cyclohexyl | H | 15 | 53–56 |
| 15 | H | H | $C_6H_5$ | $CH_3$ | 85 | (oil)[a] |
| 16 | H | H | $C_6H_5$ | $C_2H_5$ | 81 | (oil)[b] |
| 17 | H | 6-$CH_3$ | 3,4-$(CH_3O)_2C_6H_3$ | $CH_3$ | | |
| 18 | $SCH_3$ | H | 3-pyridyl | H | | |
| 19 | $CH_3$ | H | $C_6H_5$ | $CH_3$ | | |
| 20 | H | 5,7-$(CH_3)_2$ | 4-$(CH_3O)C_6H_4$ | $C_6H_5$ | | |
| 21 | H | 5,8-$(CH_3)_2$ | $C_6H_5$ | $CH_3$ | | |
| 22 | $CH_3$ | 5,8-$(CH_3)_2$ | $C_6H_5$ | $CH_3$ | | |
| 23 | H | 5-$CH_3O$ | $C_6H_5$ | 3-pyridyl | | |
| 24 | H | H | 4-$FC_6H_4$ | 4-$FC_6H_4$ | | |
| 25 | H | 6-$C_2H_5$ | 3,4-$(CH_3O)_2C_6H_3$ | $CH_3$ | | |

[a] Mass spectrum: m/z = 248
[b] Mass spectrum: m/z = 262

EXAMPLE 26

2-(3-Pyridylmethyl)-1-naphthol

A solution of 1-tetralone (5.85 g, 0.040 mole) and pyridine-3-carboxyaldehyde (4.28 g, 0.40 mol) in t-butanol (400 mL) was treated with potassium t-butoxide (8.98 g, 0.080 mol) and the resulting mixture heated at reflux for 16 hours. After cooling to room temperature, the solution was poured into stirred 1.0N hydrochloric chromatographed with 4:1 petroleum ether/ether, to provide a tan solid. This was recrystallized (cyclohexane/chloroform) to give the titel compound as white needles (5.24 g, 52%), mp 124°–125°.

The compounds of Examples 26 and 27, along with other compounds which were and can be prepared using the procedures of Examples 26 and 27, are shown in Table 5.

TABLE 5

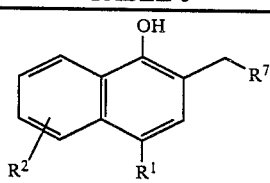

| Ex. | $R^7$ | $R^1$ | $R^2$ | YIELD % | MP (°C.) |
|---|---|---|---|---|---|
| 26 | 3-Pyridyl | H | H | 52 | 170–172 |
| 27 | 2-$HOC_6H_4$ | H | H | 52 | 124–125 |
| 28 | 4-$CH_3OC_6H_4$ | H | H | 57 | 80–81 |
| 29 | 2-$CH_3OC_6H_4$ | H | H | 66 | 89–90 |
| 30 | 4-$(C_6H_5CH_2O)C_6H_4$ | H | H | 35 | 88–89 |
| 31 | 3-$CH_3OC_6H_4$ | H | H | 36 | 55–57 |
| 32 | 3-$BrC_6H_4$ | H | H | 55 | 81–83 |
| 33 | 3-$(C_6H_5CH_2O)C_6H_4$ | H | H | 29 | 54–57 |
| 34 | 2-$BrC_6H_4$ | H | H | 65 | 85–87 |

TABLE 5-continued

Structure: 1-naphthol with OH at position 1, CH2R7 at position 2, R1 at position 4, R2 at position 5/6/7/8.

| Ex. | R7 | R1 | R2 | YIELD % | MP (°C.) |
|---|---|---|---|---|---|
| 35 | 3-FC$_6$H$_4$ | H | H | 48 | 64–65 |
| 36 | 4-CH$_3$SC$_6$H$_4$ | H | H | 59 | 82–83 |
| 37 | 3,4,5-(CH$_3$O)$_3$C$_6$H$_2$ | H | H | 52 | 121–122 |
| 38 | 2,4-(CH$_3$O)$_2$C$_6$H$_3$ | H | H | 53 | 76–77 |
| 39 | 3,4-(C$_6$H$_4$CH$_2$O)$_2$C$_6$H$_3$ | H | H | 31 | 60–61 |
| 40 | 3-(C$_6$H$_5$O)C$_6$H$_4$ | H | H | 50 | 50–52 |
| 41 | 2,3-(CH$_3$O)$_2$C$_6$H$_3$ | H | H | 35 | 140–141 |
| 42 | 3,4-(CH$_3$O)$_2$C$_6$H$_3$ | H | H | 27 | 106–107 |
| 43 | 2,4,6-(CH$_3$O)$_3$C$_6$H$_2$ | H | H | 17 | 104–105 |
| 44 | 2-Thienyl | H | H | 50 | 55–57 |
| 45 | N—CH$_3$—Pyrrol-2-yl | H | H | 59 | 85–87 |
| 46 | 2-Pyridyl | H | H | 23 | 67–68 |
| 47 | 4-(CH$_3$)$_2$NC$_6$H$_4$ | H | H | 12 | 125–127 |
| 48 | 3-CF$_3$C$_6$H$_4$ | H | H | 52 | 85–86 |
| 49 | 2-CH$_3$O—1-Naphthyl | H | H | 77 | 159–161 |
| 50 | 3,4-(Cl)$_2$NC$_6$H$_4$ | H | H | 54 | 89–90 |
| 51 | 4-Pyridyl | H | H | 50 | 157–158 |
| 52 | 3-ClC$_6$H$_4$ | H | H | 58 | 75–76 |
| 53 | 4-C$_2$H$_5$OC$_6$H$_4$ | H | H | 62 | 72–74 |
| 54 | 2-ClC$_6$H$_4$ | H | H | 79 | 83–84 |
| 55 | 2,4,5-(CH$_3$O)$_3$C$_6$H$_2$ | H | H | 27 | 153–155 |
| 56 | 2-IC$_6$H$_4$ | H | H | 62 | 81–82 |
| 57 | 2-FC$_6$H$_4$ | H | H | 66 | 75–76 |
| 58 | 4-FC$_6$H$_4$ | H | H | 56 | 74–75 |
| 59 | 4-BrC$_6$H$_4$ | H | H | 40 | 100–101 |
| 60 | 2-C$_2$H$_5$OC$_6$H$_4$ | H | H | 71 | 69–70 |
| 61 | 2-CH$_3$C$_6$H$_4$ | H | H | 65 | 81–82 |
| 62 | 3,5-(CH$_3$O)$_2$C$_6$H$_3$ | H | H | 39 | 65–67 |
| 63 | 3-CH$_3$C$_6$H$_4$ | H | H | 55 | 48–49 |
| 64 | 5-CH$_3$—Furan-2-yl | H | H | 39 | 37–39 |
| 65 | 2-(OCH$_2$COOH)C$_6$H$_4$ | H | H | 36 | 130–133 |
| 66 | 1-HO—2-Naphthyl | H | H | 27 | 172–173 |
| 67 | 4-HOC$_6$H$_4$ | H | H | 23 | 127–129 |
| 68 | 3,4-(HO)$_2$C$_6$H$_3$ | H | H | 6 | 136–139 |
| 69 | 2-naphthyl | H | H | 63 | 89–91 |
| 70 | 1-naphthyl | H | H | 60 | 132–134 |
| 71 | C$_6$H$_5$ | CH$_3$ | H | 59 | 78 |
| 72 | C$_6$H$_5$ | H | 5,7-(CH$_3$)$_2$ | 22 | 101–102 |
| 73 | C$_6$H$_5$ | H | 5-(CH$_3$O) | 78 | 116–117 |
| 74 | C$_6$H$_5$ | H | 7-(CH$_3$O) | 44 | 54–55 |
| 75 | C$_6$H$_5$ | H | 5,8-(CH$_3$)$_2$ | 44 | 90–92 |
| 76 | 3,4-(CH$_3$O)$_2$C$_6$H$_4$ | CH$_3$ | H | | |
| 77 | 3,4-(CH$_3$O)$_2$C$_6$H$_4$ | CH$_3$ | 5-(CH$_3$)$_2$ | | |
| 78 | C$_6$H$_5$ | CH$_3$ | 5-(CH$_3$O) | | |
| 79 | 4-FC$_6$H$_4$ | CH$_3$ | H | | |
| 80 | 3-pyridyl | CH$_3$ | H | | |
| 81 | C$_6$H$_5$ | CH$_3$ | 6,7-(CH$_3$O)$_2$ | | |
| 82 | 3,4-(CH$_3$O)$_2$C$_6$H$_4$ | H | 5,8-(CH$_3$)$_2$ | | |
| 83 | 3,4-Cl$_2$C$_6$H$_4$ | CH$_3$ | H | | |
| 84 | 2-furyl | H | 5,7-(CH$_3$)$_2$ | | |
| 85 | 3-CH$_3$SC$_6$H$_4$ | H | H | | |

EXAMPLE 86

2-(3-Hydroxyphenylmethyl)-1-naphthol

The compound of Example 33 (7.0 g, 0.02 mole) was combined with 10% palladium/charcoal (0.70 g) and ethanol (100 mL) in a pressure bottle. The container was pressurized with hydrogen at 50 psi and agitated at room temperature for 16 hours. It was then vented, and the reaction mixture was filtered and the catalyst rinsed with additional ethanol. The combined filtrates were evaporated, and the residue was chromatographed with 8:2 petroleum ether/ether to provide an off-white solid. This was recrystallized (carbon tetrachloride) to give the title compound (3.94 g, 77%) as a white solid, mp 100°–101°.

EXAMPLE 87

PART A 2-(2-Bromophenylmethyl)-1-benzyloxynaphthalene

A mixture of the compound of Example 34 (6.0 g, 0.019 mole), benzyl bromide (3.4 mL, 0.029 mole), potassium carbonate (5.3 g, 0.038 mole), and acetone (100 mL) was heated at reflux for 19 hours. The cooled solution was filtered and the filtrate was evaporated. The resulting oil was heated at 140°/0.5 mm to remove residual benzyl bromide, then was chromatographed with 3:1 hexane-toluene to provide the title compound (7.2 g, 94%) as a colorless oil.

PART B

2-(2-Carbethoxyphenylmethyl)-1-benzyloxynaphthalene

A solution of the product of Part A (3.00 g, 0.007 mole) in dry tetrahydrofuran (15 mL) was added to dried magnesium chips (0.22 g, 0.009 mole). A crystal of iodine was added and the mixture heated at reflux for 2 hours, then cooled to room temperature. Diethyl carbonate (4.5 mL, 0.037 mole) was added, stirring was continued for 16 hours, and the mixture was then poured into 1.0N hydrochloric acid. After isolation by extraction with ether, the crude product was chromatographed with 9:1 petroleum ether/ether, to provide the title compound (0.60 g, 20%) as an oil.

PART C

2-(2-Carbethoxyphenylmethyl)-1-naphthol

The product of Part B (0.60 g, 0.0015 mole) was hydrogenated in ethanol by the procedure of Example 86. Recrystallization of the crude product (hexane/ether) provided the title compound (0.33 g, 71%) as a waxy solid, mp 86°–88°.

EXAMPLE 88

PART A

2-(3-Bromophenylmethyl)-1-(t-butyldimethylsilyloxy)-naphthalene

A mixture of the compound of Example 32 (7.38 g, 0.024 mole), t-butyldimethylsilyl chloride (4.36 g, 0.029 mole), and imidazole (4.08 g, 0.060 mole) in N,N-dimethylformamide (20 mL) was stirred at room temperature. After 17 hours, the reaction mixture was poured into saturated aqueous sodium bicarbonate, and the crude product isolated by extraction with ether as a white, waxy solid (10.1 g, 98%), mp 72°–74°.

PART B

2-(3-Carbethoxyphenylmethyl)-1-(t-butyldimethylsilyloxy)naphthalene

The product of Part A was converted to the corresponding ethyl ester using the procedure of Part B of Example 87. The title compound was obtained as a colorless oil in 52% yield.

PART C

2-(3-Carbethoxyphenylmethyl)-1-naphthol

A solution of the product of Part B (1.00 g, 0.002 mole) in a mixture of absolute ethanol (50 mL) and 1.0N hydrochloric acid (50 mL) was heated at reflux for 5 hours. The mixture was cooled to room temperature and the crude product isolated by extraction with ethyl acetate. This material was chromatographed with 4:1 petroleum ether/ether, and the resulting solid recrystallized (hexane) to provide the title compound (0.38 g, 62%) as white crystals, mp 86°–87°.

EXAMPLE 89

2-(2-Carbethoxymethoxyphenylmethyl)-1-naphthol

A mixture of the compound of Example 65 (3.60 g, 0.012 mole), ethanol (100 mL), and sulfuric acid (0.25 mL) was heated at reflux for 4 hours. It was cooled to room temperature, then to 0°, and the title compound was collected by filtration as a tan powder (2.68 g, 66%), mp 124°–125°.

EXAMPLE 90

PART A

2-(4-Methylthiophenylmethyl)-1-(t-butyldimethylsilyloxy)naphthalene

The title compound was prepared from the compound of Example 36 using the procedure of Part A of Example 88. It was obtained as a colorless oil in quantitative yield.

PART B

2-(4-methylsulfonylphenylmethyl)-1-(t-butyldimethylsilyloxy)-naphthalene

A solution of the product of Part A (2.00 g, 0.005 mole) in glacial acetic acid (25 mL) was treated with solid sodium perborate (1.81 g, 0.011 mole) and was stirred at room temperature for 20 hours. The mixture was poured into water and the crude product isolated by extraction with ether. This material was chromatographed with 7:3 petroleum ether/ether and recrystallized (hexane) to provide the title compound (1.38 g, 63%) as white crystals, mp 109°–110°.

PART C

2-(4-Methylsulfonylphenylmethyl)-1-naphthol

A mixture of the product from Part B (1.18 g, 0.003 mole), ethanol (50 mL) and 1.0N hydrochloric acid (50 mL) was heated at reflux for 3 hours and cooled to room temperature. The crude product was isolated by extraction with ethyl acetate, and recrystallized (cyclohexane/benzene) to provide the title compound (0.75 g, 80%) as white needles, mp 144°–145°.

EXAMPLE 91

4-Bromo-2-(phenylmethyl)-1-naphthol

A solution of 2-(phenylmethyl)-1-naphthol (1.00 g, 4.3 mmole) in acetic acid (20 mL) was stirred at room temperature. A solution of bromine (0.7 g, 4.3 mmole) in acetic acid (6 mL) was added dropwise over 10 minutes. The mixture was stirred for another 5 minutes, then poured into water. The resulting solid was collected by filtration and recrystallized (cyclohexane) to provide the title compound (1.21 g, 88%) as off-white needles, mp 123°–125°.

EXAMPLE 92

4-Benzoyl-2-(phenylmethyl)-1-naphthol

A mixture of aluminum chloride (1.25 g, 9.4 mmole) in methylene chloride (25 mL) was stirred at 0° and treated dropwise with benzoyl chloride (1.1 mL, 9.4 mmole) and stirred for 5 minutes. A solution of 2-(phenylmethyl)-1-naphthol (2.0 g, 8.5 mmole) in methylene chloride (6 mL) was added dropwise over 15 minutes, and stirring was continued at 0° for 3 hours. The mixture was poured into 1.0N hydrochloric acid, and the crude product was isolated by extraction with methylene chloride. Recrystallization from toluene provided the title compound (1.15 g, 40%) as pale yellow crystals, mp 152°–155°.

EXAMPLE 93

PART A

4-Acetyl-2-(phenylmethyl)-1-acetoxynaphthalene

A mixture of aluminum chloride (5.02 g, 0.038 mole) in methylene chloride (50 mL) was stirred at 0° and treated dropwise with acetyl chloride (2.7 mL, 0.038 mole). After stirring the mixture for 10 minutes, a solution of 2-(phenylmethyl)-2-naphthol (4.00 g, 0.017 mole) in methylene chloride (10 mL) was added dropwise and stirring continued at 0° for 4 hours. The mixture was warmed to room temperature and stirred for 17 hours, then poured into 1.0N hydrochloric acid. The crude product was isolated by extraction with methylene chloride, and chromatographed (98:2 toluene/ethyl acetate). The resulting material was recrystallized (isopropanol) to provide the title compound (1.52 g, 32%) as white needles, mp 118°–120°.

PART B

4-Acetyl-2-(phenylmethyl)-1-naphthol

A solution of the compound prepared according to Part A (1.90 g, 6.0 mmole) and concentrated sulfuric acid (1.0 mL) in ethanol (150 mL) was heated at reflux for 24 hours, cooled, and poured into water. The resulting solid was collected by filtration and recrystallized (toluene) to provide the title compound (1.40 g, 84%) as a white solid, mp 139°–141°.

EXAMPLE 94

PART A 2-(Phenylmethyl)-1-methoxynaphthalene

A mixture of 2-phenylmethyl-1-naphthol (40.0 g, 0.17 mole), methyl iodide (36.4 g, 0.26 mole), potassium carbonate (35.9 g, 0.26 mole) and acetone (1000 mL) was heated at reflux with stirring for 17 hours, then cooled and filtered. The acetone was removed under vacuum, and the residue was dissolved in ethyl acetate, washed with water and brine, dried over magnesium sulfate and concentrated. The residual oil was distilled in a short-path distillation apparatus at approximately 160°–180°/0.2 torr to provide the title compound (41.5 g, 98%) as an off-white solid, mp 56°–59°.

PART B

4-Bromo-2-(phenylmethyl)-1-methoxynaphthalene

A solution of the compound of Part A (20.5 g, 0.083 mole) in acetic acid (400 mL) was stirred at room temperature and treated dropwise with a solution of bromine (13.2 g, 0.083 mole) in acetic acid (125 mL). After the mixture was stirred for an additional 15 minutes, it was diluted with water, and the crude product isolated by extraction with methylene chloride. This material was distilled at 155°–160°/0.2 torr to provide the title compound (23.25 g, 86%) as a viscous yellow oil.

PART C 4-(α-Hydroxy)-α-(2-thienyl)-methyl)-2-(phenylmethyl)-1-methoxynaphthalene A solution of the compound of Part B (2.00 g, 6.1 mmole) in dry tetrahydrofuran (20 mL) was stirred at −78° and treated dropwise with n-butyllithium (1.55M in hexane; 4.4 mL, 6.7 mmole). The mixture was stirred at −78° for one hour, then treated dropwise with a solution of thiophene-2-carboxaldehyde (0.75 g, 6.7 mmole) in dry tetrahydrofuran (10 mL). After stirring for 15 minutes, saturated aqueous ammonium chloride was added and the crude product isolated by extraction with methylene chloride. This material was chromatographed (85:15 hexane/ethyl acetate) and triturated in hexane to provide the title compound (1.90 g, 86%) as a white crystalline solid, mp 122°–124°.

PART D 4-(2-Thienylcarbonyl)-2-(phenylmethyl)-1-methoxynaphthalene

A solution of the compound of Part C (1.50 g, 4.2 mmole) in methylene chloride (90 mL) was treated with pyridinium chlorochromate (2.28 g, 10.6 mmole) and stirred at room temperature for 1.5 hours. The mixture was filtered through florisil and concentrated under vacuum to provide the crude product. This was recrystallized (hexane/1-chlorobutane) to provide the title compound (1.17 g, 79%) as a white solid, mp 111°–113°.

PART E 4-(2-Thienylcarbonyl)-2-(phenylmethyl)-1-naphthol

A mixture of the compound of Part D (0.58 g, 1.6 mmole) and pyridine hydrochloride (3.48 g, 0.03 mole) was heated at 190° for 3 hours. The cooled reaction mass was then partitioned between methylene chloride and 1.0N hydrochloric acid, and the organic phase was dried over magnesium sulfate and concentrated under vacuum. The residue was recrystallized (hexane/1-chlorobutane) to provide the title compound (0.50 g, 89%) as a pale yellow solid, mp 150°–152°.

EXAMPLE 95

PART A 3-(Phenylmethyl)-4-methoxy-1-naphthoic acid

A solution of the compound of Example 94 Part B (5.00 g, 0.015 mole) in dry tetrahydrofuran (50 mL) was cooled to −78° and treated dropwise with n-butyllithium (1.55M in hexane; 10.9 mL, 0.017 mole). The mixture was stirred at −78° for 45 minutes, and a stream of gaseous carbon dioxide was directed onto the surface of the stirred solution. The cooling bath was removed from the reaction vessel and the addition of carbon dioxide was continued for 5 minutes. The mixture was then poured into 1.0N hydrochloric acid, and the crude product isolated by extraction with methylene chloride. This was recrystallized (methylcyclohexane) to provide the title compound (4.0 g, 90%) as a pale yellow solid, mp 146°–148°.

PART B 3-(Phenylmethyl)-4-hydroxy-1-naphthoic acid

Using the procedure of Example 13 Part C, the compound of Part A was converted to the title compound, which was recrystallized (acetonitrile) to provide a tan solid (68%), mp 203°–206° (decomposes).

EXAMPLE 96

3-(Phenylmethyl)-4-hydroxy-1-naphthoic acid ethyl ester

A solution of the compound of Example 95 (2.55 g, 9.2 mmole) and concentrated sulfuric acid (3 drops) in ethanol (125 mL) was heated at reflux for 80 hours. The mixture was cooled and diluted with water, and the crude product was isolated by extraction with ethyl acetate. This was chromatographed (9:1 hexane/ethyl acetate) and recrystallized (hexane) to provide the title compound (1.74 g, 62%) as white needles, mp 79°-80°.

EXAMPLE 97

PART A 3-(Phenylmethyl)-4-methoxy-1-naphthamide

A mixture of the compound of Example 95 Part A (3.00 g, 10.3 mmole), oxalyl chloride (6.50 g, 0.051 mole) and benzene (30 mL) was stirred at room temperature for 20 hours, and concentrated under vacuum. The residue was dissolved in dry tetrahydrofuran (30 mL) and added dropwise with stirring to aqueous ammonia (28%) which was cooled on an ice/acetone bath. Stirring was continued for 6 hours, while the reaction mixture was allowed to warm to room temperature. The ammonia and tetrahydrofuran were then removed under vacuum, and the product was isolated by extraction with ethyl acetate and methylene chloride. After recrystallization (isopropanol), the title product was obtained (2.69 g, 87%) as white needles, mp 199°-201°.

PART B 3-(Phenylmethyl)-4-hydroxy-1-naphthamide

Using the procedure of Example 94 Part E, the compound of Part A was converted to the title compound, which was obtained in 56% yield as a white solid (mp 219°-220° dec.) after recrystallization from toluene.

EXAMPLE 98

PART A

4-Phenyl-2-(phenylmethyl)-1-methoxynaphthalene

A solution of the compound of Example 94 Part B (5.00 g, 15.3 mmole) and bis-(1,3-diphenylphosphino)-propane nickel(II) chloride (0.40 g, 0.74 mmole) in dry ether was stirred at 0°. Phenylmagnesium chloride (2.0M in ether; 9.5 mL, 19.0 mmole) was added dropwise, and the mixture was stirred at room temperature for 2 hours. The mixture was then poured into 1.0N hydrochloric acid, and the crude product was isolated by extraction with methylene chloride. This was chromatographed to provide the title product (4.26 g, 86%) as a white solid. A small sample recrystallized from hexane melted at 103°-105°.

PART B

4-Phenyl-2-(phenylmethyl)-1-naphthol

Using the procedure of Example 13 Part C, the compound of Part A was converted to the title compound, which was obtained as a white solid (73% yield, mp 132°-134°) after recrystallization from methylcyclohexane.

EXAMPLE 99

PART A

4-Methoxy-3-(phenylmethyl)-naphthalene-1-sulfonic acid

The product of Example 94 Part A (3.0 g, 0.012 mole) was added in portions to concentrated sulfuric acid (10 ml) at −10°. The mixture was stirred at −10° for 2 hours and poured into water. Sodium bicarbonate (1.0 g) was added, and the crude product was isolated by extraction with ethyl acetate. The title compound (2.0 g, 52%) was obtained as a brown oil after chromatography (1:1 hexane/ethyl acetate; then 99:1 ethyl acetate/acetic acid; then methanol).

PART B

4-Methoxy-3-(phenylmethyl)-naphthalene-1-sulfonyl chloride

A mixture of the product of Part A (1.80 g, 5.5 mmole), thionyl chloride (10 mL), and N,N-dimethylformamide (1 drop) was heated at reflux for one hour. The excess thionyl chloride was removed at reduced pressure to provide the title compound (2.3 g) as a brown oil, which was used without further purification.

PART C

4-Methoxy-3-(phenylmethyl)-naphthalene-1-sulfonamide

A solution of the product of Part B (4.65 g, 0.013 mole) in tetrahydrofuran was added dropwise to a solution of aqueous ammonia (28%, 125 ml). After 10 minutes, the solvent was removed at reduced pressure, and the aqueous residue was acidified. The crude product was isolated by extraction with ethyl acetate. Chromatography (1:1 hexane/ethyl acetate) and recrystallization (1-chlorobutane) provided the title compound (1.0 g, 46%) as a white solid, mp 159°-161°.

PART D

4-Aminosulfonyl-2-(phenylmethyl)-1-naphthol

Using the procedure of Example 13, Part C, the product of Part C was converted in 85% yield to the title compound, mp 167°-168°.

The compounds of Examples 86-99, along with other compounds which were or can be prepared using one of the methods described in Examples 86-99 or in the general synthetic discussions are shown in Table 6.

TABLE 6

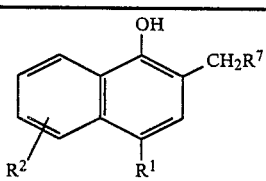

| Ex. No. | $R^1$ | $R^2$ | $R^7$ | YIELD % | MP (°C.) |
|---|---|---|---|---|---|
| 86 | H | H | 3-HOC$_6$H$_4$ | 77 | 100-101 |
| 87 | H | H | 2-(C$_2$H$_5$OOC)C$_6$H$_4$ | 71 | 86-88 |
| 88 | H | H | 3-(C$_2$H$_5$OOC)C$_6$H$_4$ | 62 | 86-87 |
| 89 | H | H | 2-(OCH$_2$COOC$_2$H$_5$)C$_6$H$_4$ | 66 | 124-125 |
| 90 | H | H | 4-(CH$_3$SO$_2$)C$_6$H$_4$ | 80 | 144-145 |
| 91 | Br | H | C$_6$H$_5$ | 88 | 123-125 |

TABLE 6-continued

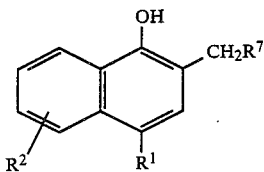

| Ex. No. | R¹ | R² | R⁷ | YIELD % | MP (°C.) |
|---|---|---|---|---|---|
| 92 | O=CC₆H₅ | H | C₆H₅ | 40 | 152–155 |
| 93 | O=CCH₃ | H | C₆H₅ | 84 | 139–141 |
| 94 | O=C-(2-thienyl) | H | C₆H₅ | 89 | 150–152 |
| 95 | COOH | H | C₆H₅ | 68 | 203–206 (dec) |
| 96 | COOC₂H₅ | H | C₆H₅ | 62 | 79–80 |
| 97 | CONH₂ | H | C₆H₅ | 56 | 219–220 (dec) |
| 98 | C₆H₅ | H | C₆H₅ | 73 | 132–134 |
| 99 | SO₂NH₂ | H | C₆H₅ | 85 | 167–168 |
| 100 | CH₃ | 5,8-(CH₃)₂ | 3,4-(CH₃O)₂C₆H₃ | | |
| 101 | O=C-(3-pyridyl) | H | 3-pyridyl | | |
| 102 | NHCCH₃ (O=) | H | C₆H₅ | | |
| 103 | NHSO₂CH₃ | H | C₆H₅ | | |
| 104 | NHSO₂CF₃ | H | C₆H₅ | | |
| 105 | SO₂CH₃ | H | C₆H₅ | | |
| 106 | Cl | H | C₆H₅ | 21% | 99–101 |
| 107 | O=CCH₂CH₂CH₃ | H | 3,4-(CH₃O)₂C₆H₃ | | |
| 108 | O=C-(2-furyl) | 7-CH₃O | C₆H₅ | | |
| 109 | Br | H | 3,4-(CH₃O)₂C₆H₅ | | |
| 110 | CONHCH₃ | H | C₆H₅ | | |
| 111 | CON(CH₃)₂ | H | C₆H₅ | 12% | 208–210 |
| 112 | CON(CH₂)₄ | H | C₆H₅ | | |
| 113 | NH₂·HCl | H | C₆H₅ | | |
| 114 | NHCH₃ | H | C₆H₅ | | |
| 115 | SCH₃ | H | C₆H₅ | | |
| 116 | COOCH₃ | H | C₆H₅ | | |

EXAMPLE 117

PART A

Ethyl 1-hydroxy-2-naphthalenepentanoate

The title compound was prepared as reported by G. Xi, X. Guo, and R. Chen, *Yaoxue Xuebao* 15, 548 (1980).

PART B 2-(5-Hydroxypentyl)-1-naphthol

A solution of the product of Part A (2.00 g, 0.007 mole) in dry tetrahydrofuran (10 mL) was added dropwise to a mixture of lithium aluminum hydride (0.28 g, 0.007 mole) in dry tetrahydrofuran (20 mL) at 0°. The mixture was heated at reflux for 30 minutes, then cooled to room temperature. Water (0.28 mL), then 3.0N aqueous sodium hydroxide (0.28 mL), then water (0.60 mL) were added, and the mixture wwas stirred at room temperature for 10 minutes, then filtered. The filtrate was diluted with water and extracted with ethyl acetate. The resulting material was chromatographed with 7:3 toluene/ethyl acetate to provide the title compound (1.10 g, 65%) as a waxy solid, mp 43°–46°.

EXAMPLE 118

PART A 2-(2-Propenyl)-1-naphthol

The title compound was prepared by the procedure of J. St. Pyrek, O. Achmatowicz, and A. Zamojski, *Tetrahedron* 33, 673 (1977).

PART B 2-(2-Propenyl)-1-benzyloxynaphthalene

A mixture of the product of Part A (12.80 g, 0.070 mole), benzyl bromide (10.75 mL, 0.090 mole), and potassium carbonate (19.20 g, 0.139 mole) in acetone (150 mL) was heated at reflux for 3 hours. The cooled solution was filtered and the filtrate evaporated. The residual oil was distilled to provide the title compound (12.91 g, 68%) as a pale yellow liquid, bp 150°–151° (0.1 torr).

PART C 2-(3-Hydroxypropyl)-1-benzyloxynaphthalene

A solution of borane (1.0M in tetrahydrofuran; 100 mL, 0.100 mole) was treated at 0° with a solution of 2-methyl-2-butene (2.0M in tetrahydrofuran; 100 mL, 0.200 mole) over 40 minutes, and the resulting solution stirred at 0° for 2 hours. A solution of 2-(2-propenyl)-1-benzyloxynaphthalene (27.40 g, 0.100 mole) in dry tetrahydrofuran (50 mL) was added over 25 minutes, and stirring was continued for 40 minutes. Water (4.0 mL) was then added, followed by 3.0M aqueous sodium hydroxide (34 mL), followed by 30% aqueous hydrogen peroxide (34 mL). After the mixture was warmed to room temperature, it was extracted with ether. The residue was chromatographed with 1:1 ether/hexane and recrystallized (cyclohexane) to provide the title compound (16.10 g, 55%) as a white solid, mp 80°–81°.

PART D 2-(3-Hydroxypropyl)-1-naphthol

The product of Part C (1.00 g, 0.003 mole) was combined with 10% palladium/charcoal (0.20 g) and ethanol (35 mL) in a pressure bottle. The container was pressurized with hydrogen at 50 psi, and agitated at room temperature for 4 hours. It was then vented, and the reaction mixture was filtered and the catalyst rinsed with additional ethanol. The combined filtrates were evaporated, and the residue was recrystallized (cyclohexane) to give the title compound (0.52 g, 74%) as off-white crystals, mp 85°–86°.

EXAMPLE 119

2-(5-Hydroxy-5-methylhexyl)-1-naphthol

A solution of the product of Example 117 Part A (2.00 g, 0.007 mole) in dry tetrahydrofuran (20 mL) was stirred at 0° and treated with methyllithium (1.5M in ether; 20 mL, 0.030 mole) over 10 minutes. Stirring was continued for 1.25 hours at 0°, then for 1.5 hours at room temperature. The mixture was again cooled to 0°, and treated with saturated ammonium chloride solution, then warmed to room temperature and extracted with ether. The crude product was recrystallized (toluene) to give the title compound (1.70 g, 89%) as white crystals, mp 101°–102°.

EXAMPLE 120

2-(5-Methyl-4-hexenyl)-1-naphthol

A solution of the compound of Example 119 (0.45 g, 0.002 mole) and p-toluenesulfonic acid (4–5 crystals) in toluene (20 mL) was heated at reflux with azeotropic removal of water. After 18 hours, the cooled solution was washed with saturated aqueous sodium bicarbonate and evaporated to provide the title compound (0.45 g, 100%) as an oil; mass spectrum: m/z 240.

EXAMPLE 121

PART A 2-(4-Chlorobutyryl)-1-naphthol

A mixture of 1-naphthol (15.14 g, 0.105 mole), 4-chlorobutyric acid (9.90 mL, 0.100 mole), and boron trifluoride etherate (75 mL) was heated on a steam bath for 4 hours. The mixture was then treated slowly with 100 mL of water, and heating continued for 30 minutes. The mixture was poured into water, stirred, and the solution decanted. The residue was triturated with water, then crystallized from ethanol to provide the title compound (9.50 g, 38%) as a pale green solid, mp 73°–79°.

PART B 2-(4-Chlorobutyl)-1-naphthol

A mixture of granular zinc (6.50 g, 0.099 mole), mercury (II) chloride (0.2 g), concentrated hydrochloric acid (0.6 mL), and water (10 mL) was stirred at room temperature for 30 minutes, then washed with water by decantation. To the solid was added the product of Part A (5.00 g, 0.020 mole), ethanol (125 mL), and concentrated hydrochloric acid (35 mL). The mixture was stirred at reflux overnight, cooled, and the supernatant was diluted with water. The crude product was isolated by extraction with ethyl acetate and chromatographed with 98:2 hexane/ether. The title compound was obtained as a light brown oil (2.00 g, 43%), mass spectrum m/z=234, 236.

EXAMPLE 122

PART A 2-(2-Propenyl)-1-t-butyldimethylsilyloxynaphthalene

A mixture of 2-(2-propenyl)-1-naphthol (Example 118 Part A; 101.9 g, 0.550 mole), t-butyldimethylsilyl chloride (100.0 g, 0.660 mole), and imidazole (93.6 g, 1.375 mole) in N,N'-dimethylformamide was stirred at room temperature for 6.5 hours. It was then poured into saturated aqueous sodium bicarbonate, and the crude product isolated by extraction with hexane. The residue was distilled at reduced pressure to provide the title compound (155.2 g, 95%), bp 135°–140° (0.1 torr).

PART B 2-(3-Hydroxypropyl)-1-t-butyldimethylsilyloxy-naphthalene

A solution of the product of Part A (29.80 g, 0.100 mole) in dry tetrahydrofuran was treated at 0° with borane (1.0M in tetrahydrofuran; 38 mL, 0.038 mole) over 30 minutes. Water (7.0 mL) was added, followed by 3.0N aqueous sodium hydroxide (14 mL), after which the reaction flask was again cooled to 0°. 30% Aqueous hydrogen peroxide (14 mL) was added over 10 minutes, and the mixture was warmed to room temperature, stirred for 30 minutes, and heated to 50° with a warm water bath. After 30 minutes, the cooled mixture was diluted with water, and the crude product extracted with ether. The residue was recrystallized (cyclohexane) to provide the title compound (22.70 g, 72%) as a white solid, mp 91°–93°.

PART C 2-(3-Bromopropyl)-1-t-butyldimethylsilyloxynaphthalene

A solution of the product of Part B (15.80 g, 0.050 mole) and carbon tetrabromide (33.10 g, 0.100 mole) in ether (150 mL) was treated at room temperature with a solution of triphenylphosphine (26.20 g, 0.100 mole) in ether (110 mL). After 2.75 hours, the mixture was filtered, and the filtrate was evaporated. The residue was chromatographed with petroleum ether to provide the title compound (18.00 g, 95%) as a colorless oil.

PART D 2-(3-Bromopropyl)-1-naphthol

A solution of the product of Part C (2.60 g, 0.007 mole) in ethanol (50 mL) was mixed with 1.0N aqueous hydrochloric acid (30 mL) and heated at reflux. After 3.5 hours, the mixture was cooled to room temperature, and diluted with water. The crude product was isolated by extraction with methylene chloride, and chromatographed with 9:1 hexane/ethyl to acetate provide an orange solid. This was recrystallized from hexane to give the title compound (0.51 g, 28%) as a tan solid, mp 53°–55°.

EXAMPLE 123

PART A 3-(1-t-Butyldimethylsilyloxy-2-naphthyl)propylisothiourea hydrochloride A mixture of the product of Example 122 Part C (1.55 g, 0.004 mole), thiourea (0.31 g, 0.004 mole), and absolute ethanol (8.0 mL) was heated at reflux for 7 hours. The cooled solution was treated with water (5.0 mL), cooled to 0°, and treated with concentrated hydrochloric acid (5.0 mL). The precipitated solid was isolated by filtration, rinsed with water and air-dried to provide the title compound (1.45 g, 86%) as a white powder, mp 190°–194°.

PART B 3-(1-Hydroxy-2-naphthyl)-propylisothiourea hydrochloride

A mixture of the product of Part A (0.65 g, 0.002 mole), ethanol (6 mL), and 1.0N aqueous hydrochloric acid (10 mL) was heated at reflux for 2 hours. After cooling, the ethanol was removed by evaporation at reduced pressure, and the solid collected by filtration and washed with water. The title compound was obtained (0.42 g, 84%) as a white powder, mp 184°–188°.

EXAMPLE 124

2-(3-Mercaptopropyl)-1-naphthol

A mixture of the product from Example 123 Part B (0.90 g, 0.002 mole), ethanol (4.0 mL), and 4.0N aqueous sodium hydroxide (10.0 mL) was heated at reflux for 2 hours. The cooled solution was acidified with concentrated hydrochloric acid and extracted with methylene chloride. The crude product was chromatographed with 97:3 hexane/ethyl acetate to provide the title compound (0.50 g, 97%) as an orange oil. Mass spectrum: m/z 218.

EXAMPLE 125

2-[3-(N-Pyrrolidino)-propyl]-1-naphthol hydrochloride

A mixture of the product of Example 122 Part C (2.00 g, 0.005 mole), pyrrolidine (4.40 mL, 0.053 mole), potassium carbonate (1.10 g, 0.008 mole), and acetonitrile (20 mL) was heated at reflux for 16 hours. The cooled solution was filtered, and the filtrate chromatographed with 98:2 methylene chloride/methanol chloride to give a light tan oil. This was dissolved in ether, treated with ethereal hydrogen chloride, and stirred at room temperature. The precipitated solid was isolated by filtration, washed with ether, washed further with a small amount of acetonitrile, and air-dried to provide the title compound (1.17 g, 76%) as a white powder, mp 198°–201°.

EXAMPLE 126

2-(3-Aminopropyl)-1-naphthol hydrochloride

A solution of the product of Example 122 Part C (2.00 g, 0.005 mole) in N,N-dimethylformamide (3.4 mL) was added over a period of 5 minutes to a stirred suspension of sodium azide (0.41 g, 0.006 mole) in N,N-dimethylformamide (4 mL) at 105°. After the mixture was stirred for 4 hours, it was cooled to room temperature, poured into water, and extracted with methylene chloride. The residue was stirred in a mixture of ethanol (100 mL) and 1.0N hydrochloric acid (100 mL) at reflux for 2 hours. The cooled mixture was extracted with methylene chloride, and the crude product was hydrogenated using the procedure of Example 110 Part D in 17% chloroform/ethanol. The resulting material was boiled in acetonitrile, then isolated by filtration to provide the title compound (0.87 g, 73%) as a tan solid, mp 213°–218° (decomposes).

EXAMPLE 127

PART A 2-(4-Chlorobutyl)-1-methoxynaphthalene

A solution of N,N,N',N'-tetramethylenediamine (18.12 mL, 0.120 mole) in cyclohexane (36 mL) was treated with n-butyllithium (1.55M in hexane; 79.8 mL, 0.123 mole) at room temperature. A solution of 1-methoxynaphthalene (17.4 mL, 0.120 mole) in cyclohexane (20 mL) was added over 30 minutes, and the resulting solution was stirred for 1.5 hours. It was then cooled to 0°, and 1-bromo-4-chlorobutane (27.0 mL, 0.234 mole) was added over 15 minutes. The mixture was warmed to room temperature and stirred for 17 hours, then poured into saturated aqueous ammonium chloride and extracted with ethyl acetate. The crude product was chromatographed with 98:2 hexane/ether to provide the title compound (11.60 g, 39%) as a pale yellow oil.

PART B

Diethyl 4-(1-methoxy-2-naphthyl)butylphosphonate

The product from Part A (5.00 g, 0.020 mole) was dissolved in acetone (50 mL) and treated with sodium iodide (6.00 g, 0.040 mole). The solution was heated at reflux for 3.5 hours, cooled to room temperature, and extracted with methylene chloride. The resulting material was combined with triethyl phosphite (15 mL) and stirred at 150° for 17 hours. After cooling, the excess triethyl phosphite was removed under reduced pressure, and the residue was chromatographed with ethyl acetate to provide the title compound (3.90 g, 56%) as a pale yellow oil.

PART C

Diethyl 4-(1-hydroxy-2-naphthyl)butylphosphonate

A solution of diethyl 4-(1-methoxy-2-naphthyl)butylphosphonate (5.50 g, 0.016 mole) in methylene chloride (80 mL) was stirred at −78°, and treated with boron tribromide (1.0M in methylene chloride; 24.0 mL, 0.024 mole) over 20 minutes. Stirring was continued for 2 hours at this temperature, then at room temperature for 16 hours. Water (80 mL) was added, and the mixture was extracted with ether. The organic layer was extracted with 1.0N aqueous sodium hydroxide, the aqueous layer was acidified with concentrated hydrochloric acid, and the crude product was isolated from this by extraction with ether. The residue was recrystallized (hexane) to provide the title compound (2.10 g, 40%) as a white solid, mp 90°–91°.

EXAMPLE 128

PART A 2-(3-p-Toluenesulfonyloxypropyl)-1-benzyloxynaphthalene

A solution of the product of Example 118 Part C (9.10 g, 0.031 mole) in pyridine (150 mL) was stirred at 0° and treated with p-toluenesulfonyl chloride (6.70 g, 0.035 mole), then stirred for 16 hours at room temperature. The solution was poured into water, and the mixture extracted with ethyl acetate. The resulting oil was chromatographed with 4:1 hexane/ether to provide the title compound (3.20 g, 23%) as an oil.

PART B 2-(4,4-bis-Carbethoxybutyl)-1-benzyloxynaphthalene

Sodium (0.08 g, 0.004 mole) was dissolved in ethanol (5 mL) and the resulting solution was treated with diethyl malonate (0.51 mL, 0.004 mole) and stirred at room temperature for 10 minutes. A solution of the product from Part A (1.00 g, 0.002 mole) in ethanol (5 mL) was added, and the mixture was stirred at reflux for 3.5 hours. The cooled solution was poured into 1.0N hydrochloric acid, and the crude product was isolated by extraction with ethyl acetate. This was chromatographed with 9:1 petroleum ether/ether to provide the title compound (0.70 g, 72%) as an oil.

PART C

3-[(1-Hydroxy-2-naphthyl)propyl]propanedioic acid, diethyl ester

Using the procedure of Example 118, Part D the product of Part B was converted in 84% yield to the title compound, an orangish oil. Mass spectrum: m/z 344.

EXAMPLE 129

1-Hydroxy-2-naphthalenebutyronitrile

A mixture of the product of Example 122 Part C (3.79 g, 0.010 mole), potassium cyanide (0.72 g, 0.011 mole), ethanol (15 mL) and water (2 mL) was heated at reflux for 20 hours. The cooled mixture was poured into water and extracted with ethyl acetate. The crude product was chromatographed with 1:1 ether/hexane and recrystallized (cyclohexane/toluene) to provide the title compound (0.73 g, 35%) as a white solid, mp 76°–78°.

EXAMPLE 130

2-(3-Methoxypropyl)-1-naphthol

A suspension of sodium hydride (60% in mineral oil; 0.28 g, 0.007 mole) in dry tetrahydrofuran (5 mL) was stirred at 0°. A solution of the product of Example 122 Part B (2.00 g, 0.006 mole) was added slowly, and the mixture warmed to room temperature. Methyl iodide (0.8 mL, 0.013 mole) was added, the mixture was stirred for 3 hours, then was poured into 1.0N hydrochloric acid. The crude material was isolated by extraction with methylene chloride, dissolved in a mixture of methanol (20 mL) and 1.0N hydrochloric acid (20 mL), and heated at reflux for 20 hours. The cooled solution was extracted with methylene chloride, and the residue was chromatographed with 9:1 petroleum ether/ether to provide the title compound (0.90 g, 66%) as a colorless oil. Mass spectrum: m/z 216.

EXAMPLE 131

PART A

Ethyl 1-benzyloxy-2-naphthalenepentanoate

Using the procedure of Example 87 Part A, the compound of Example 117 Part A was converted into the title compound, a pale yellow oil, in 100% yield.

PART B

1-Benzyloxy-2-naphthalenepentanoic acid

A mixture of the compound of Part A (6.10 g, 0.017 mole), ethanol (10 ml), and 1.0N aqueous sodium hydroxide was heated at reflux for 17 hours and cooled to 0°. Concentrated hydrochloric acid was added until the mixture was acidic, then stirring was continued for 3 days. The crude product was isolated by filtration, dissolved in hot isopropanol, filtered and concentrated. The residue was recrystallized (cyclohexane-hexane) to yield the title compound (3.7 g, 65%) as a tan solid, mp 70°–77°.

PART C

1-Benzyloxy-2-naphthalenepentanamide

A mixture of the product of Part B (1.00 g, 3.0 mmole), oxalyl chloride (1.3 mL, 15.0 mmole) and benzene (10 mL) was stirred at room temperature for 16 hours. The mixture was concentrated under vacuum to provide a tan, viscous oil which was dissolved in dry tetrahydrofuran (8 mL) and added dropwise with stirring to aqueous ammonia (28%, 50 mL) at −12°. The mixture was warmed to room temperature and stirred for 6 hours, then concentrated under vacuum to remove the ammonia and tetrahydrofuran. The crude product was isolated by extraction with ethyl acetate as a yellow glass (1.0 g, 100%).

PART D

1-Hydroxy-2-naphthalenepentanamide

The compound of Part C (1.0 g, 3.0 mmole) was hydrogenated in ethanol by the procedure of Example 86. Recrystallization of the crude product (cyclohexane/ethylacetate) provided the title compound (0.35 g, 48%) as a white solid, mp 75°–78°.

EXAMPLE 132

1-(5-[1-Hydroxy-2-naphthyl]-1-oxopentyl)-pyrrolidine

A mixture of the compound of Example 131 Part B (1.00 g, 3.0 mmole), oxalyl chloride (1.3 mL, 15.0 mmole) and benzene (10 mL) was stirred at room temperature for 21 hours and concentrated under vacuum. The residue was dissolved in methylene chloride (10 mL) and added dropwise to a stirred solution of pyrrolidine (0.53 mL, 6.3 mmole) in methylene chloride (10 mL) at 0°. After 6.5 hours, the mixture was diluted with ether, washed with water and 1.0N hydrochloric acid, then dried over magnesium sulfate and concentrated under vacuum. The crude material was hydrogenated using the procedure of Example 86. Recrystallization of the crude product (ethyl acetate/ethanol) provided the title compound (0.63 g, 76%) as an off-white solid, mp 166°–160°.

The compounds of Examples 117 to 132, as well as other compounds which can be prepared using one of the procedures described in Examples 117 to 132 or in the general synthetic discussion, are shown in Table 7.

TABLE 7

| Ex. No. | n | $R^1$ | $R^2$ | $R^6$ | YIELD % | MP(°C.) |
|---|---|---|---|---|---|---|
| 117 | 5 | H | H | OH | 65 | 43–46 |
| 118 | 3 | H | H | OH | 74 | 85–86 |
| 119 | 4 | H | H | $C(CH_3)_2OH$ | 89 | 101–102 |
| 120 | 3 | H | H | $CH=C(CH_3)_2$ | 100 | (oil)$^a$ |
| 121 | 4 | H | H | Cl | 43 | (oil)$^b$ |
| 122 | 3 | H | H | Br | 28 | 53–55 |
| 123 | 3 | H | H | $SC(NH)NH_2 \cdot HCl$ | 84 | 184–188 |
| 124 | 3 | H | H | SH | 97 | (oil)$^c$ |
| 125 | 3 | H | H | $N(CH_2)_4 \cdot HCl$ | 76 | 198–201 |
| 126 | 3 | H | H | $NH_2 \cdot HCl$ | 73 | 213–218(d) |
| 127 | 4 | H | H | $P(O)(OC_2H_5)_2$ | 40 | 90–91 |
| 128 | 3 | H | H | $CH(COOC_2H_5)_2$ | 84 | (oil)$^d$ |
| 129 | 3 | H | H | CN | 35 | 76–78 |
| 130 | 3 | H | H | $OCH_3$ | 66 | (oil)$^e$ |
| 131 | 4 | H | H | $CONH_2$ | 48 | 75–78 |
| 132 | 4 | H | H | $CON(CH_2)_4$ | 76 | 166–169 |
| 133 | 3 | $CH_3$ | H | I | | |
| 134 | 3 | H | 5,8-$(CH_3)_2$ | $CON(CH_3)_2$ | | |
| 135 | 4 | Br | H | cyclohexyl | | |
| 136 | 3 | $C_6H_5$ | 6-$CH_3$ | $P(O)OCH_3)_2$ | | |
| 137 | 4 | $CH_3$ | H | $\overset{O}{\underset{\|}{S}}OCH_3$ | | |
| 138 | 3 | $\overset{O}{\underset{\|}{C}}CH_3$ | H | OH | | |

$^a$mass spec m/z = 240
$^b$mass spec m/z = 234, 236
$^c$mass spec m/z = 218
$^d$mass spec m/z = 344
$^e$mass spec m/z = 216

DOSAGE FORMS

The lipoxygenase inhibitors of this invention can be administered to treat inflammation, including but not limited to rheumatoid arthritis, dermatoses, allergy, chronic obstructive lung diseases such as asthma and bronchitis, or psoriasis. In addition, the compounds of this invention may also be useful in the treatment of osteoarthritis. They may be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms, by inhalation in the form of a nasal spray or lung inhaler, or topically as an ointment, cream or lotion.

Gelatin capsules contain the active ingredient and powdered carriers, such as lactose, sucrose mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl or propyl-paraben, and chlorobutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 50 milligrams of powdered active ingredient, 175 milligrams of lactose, 24 milligrams of talc, and 6 milligrams of magnesium stearate.

SOFT GELATIN CAPSULES

A mixture of active ingredient in soybean oil is prepared and injected by means of a positive displacement pump into gelatin to form soft gelatin capsules containing 50 milligrams of the active ingredient. The capsules are washed in petroleum ether and dried.

TABLETS

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 225 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is sterilized by commonly used techniques.

SUSPENSION

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

NASAL SPRAY

An aqueous solution is prepared such that each 1 milliliter contains 10 milligrams of active ingredient, 1.8 milligrams methylparaben, 0.2 milligrams propylparaben and 10 milligrams methylcellulose. The solution is dispensed into 1 milliliter vials.

LUNG INHALER

A homogeneous mixture of the active ingredient in polysorbate 80 is prepared such that the final concentration of the active ingredient will be 10 milligrams per container and the final concentration of polysorbate 80 in the container will be 1% by weight. The mixture is dispensed into each can, the valves are crimped onto the can and the required amount of dichlorotetrafluoroethane is added under pressure.

TOPICAL FORMULATION

An ointment for topical administration may be prepared by adding the active ingredient to a mixture of 48% by weight white petrolatum, 10% liquid petrolatum, 8% glycerol monostearate, 3% isopropyl myristate and 20% lanolin at 70° C. After thorough mixing, a warm solution of methyl and propyl parabens in water containing sodium acetone bisulfite is added such that the final concentrations of each paraben is 0.15%, of water is 8% and of sodium acetone bisulfite is 0.5%. The mixture is stirred until it has reached room temperature.

USE

The compounds of this invention have been shown to inhibit 5-lipoxygenase in an in vitro test system using rat basophilic leukemia (RBL-1) cells as the source of enzyme. The test method is a modification of the procedures developed by Jakschik et al (*Prostaglandins*, 16, 733–748 (1978), *Biochem, Biophys. Res. Comm.*, 95, 103–110 (1980), 102, 624–629 (1981). The 10,000 xg supernatant from homogenized RBL-1 cells was incubated with drug in a pH 7.0 phosphate buffer for five minutes. $^{14}$C-arachidonic acid was added to initiate the reaction which was allowed to continue at 37° C. for two minutes. The reaction was stopped by freezing in a dry ice/ethanol slurry, and the 5-lipoxygenase products were separated from the substrate on silica gel columns. The amount of individual lipoxygenase products produced was determined and the percent inhibition calculated.

The enzyme 5-lipoxygenase catalyzes the first reaction in the biosynthesis of the potent biological mediators, the leukotrienes ($LTB_4$, $LTC_4$, $LTD_4$, $LTE_4$) from arachidonic acid. Collectively $LTC_4$, $LTD_4$, and $LTE_4$ are the materials which used to be known as slow reacting substance of anaphylaxis (SRS-A) before they were chemically characterized as leukotrienes. $LTC_4$ and $LTD_4$ are extremely potent mediators of anaphylaxis and seem to be particularly effective at reducing the air flow in peripheral airways. In animal models, reduction of the synthesis of SRS-A leads to a reduction in the symptoms following an allergic challenge. $LTB_4$ is a potent leukocyte chemotactic factor and aggregating agent. Polymorphonuclear leukocytes (PMN) are particularly sensitive to activation by $LTB_4$. Reduction of the synthesis of $LTB_4$ by blocking 5-lipoxygenase should reduce the influx of PMN to an inflamed site-either an arthritic joint or a psoriatic lesion. Elevated levels of $LTB_4$ have been found in both the synovial fluid of rheumatoid patients and in the plaque area of psoriasis patients. Thus a 5-lipoxygenase inhibitor, by reducing the production of these potent biological mediators, is useful for the treatment of inflammation, chronic obstructive lung diseases such as asthma and bronchitis, and skin diseases such as psoriasis.

Some of the 5-lipoxygenase inhibiting compounds of this invenion were found to inhibit arachidonic acid-induced ear edema. This in vivo assay is a modification of the procedure described by Young et al. (*J. Invest. Derm.*, 80, 48–52, 1983) and indicates a specific use in the treatment of skin diseases such as psoriasis.

In addition, two of the 5-lipoxygenase inhibiting compounds of this invention were tested in vitro using sensitized guinea pig pulmonary parenchymal strips and found to be active. This test utilizes procedures described by Fleish et al. (*J. Pharm. Exp. Therap.*, 221, 146-151, 1982) and Drazen et al. (*Proc. Acad. of Sci. USA*, 77, 4354–4358, 1980) and is indicative of anti-asthmatic potential.

What is claimed is:

1. A pharmaceutical composition comprising a suitable pharmaceutical carrier and a 5-lipoxygenase inhibiting amount of a compound having the formula:

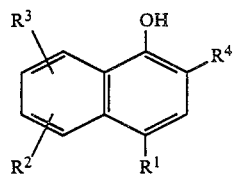

wherein
$R^1$ is H;
$R^2$ and $R^3$ independently are H, $CH_3$, $C_2H_5$, $OCH_3$, or $OC_2H_5$;
$R^4$ is

$R^7$ is $C_3$–$C_8$ cycloalkyl

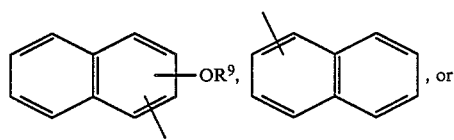

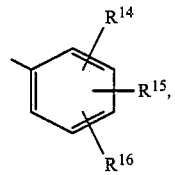

$R^9$ is H or $C_1$–$C_4$ alkyl;
$R^{12}$ and $R^{13}$ independently are H, $C_1$–$C_4$ alkyl, or together are $(CH_2)_{4-5}$;
$R^{14}$ is H, $C_1$–$C_4$ alkyl, $OR^9$, O-phenyl, O-benzyl, $CF_3$, Cl, Br, I, $N(R^{12})(R^{13})$, or $S(O)_wR^9$ where w is 0–2 with the proviso that is w is 1 then $R^9$ is not H; and
$R^{15}$ and $R^{16}$ are independently H, $C_1$–$C_4$ alkyl, $OR^9$, O-benzyl, F or Cl, and
$R^{21}$ is H,
or a pharmaceutically suitable salt thereof.

2. The composition of claim 1 wherein $R^7$ is

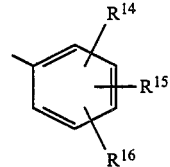

3. The composition of claim 2 wherein $R^{14}$ is H, $C_{1-4}$ alkyl, $OR^9$, Cl, Br, or I; and $R^{15}$ and $R^{16}$ are independently H, $OR^9$, F, or Cl.

4. The composition of claim 1 wherein the compound is 2-(3-bromophenylmethyl)-1-naphthol.

5. The composition of claim 1 wherein the compound is 2-(2-fluorophenylmethyl)-1-naphthol.

6. The composition of claim 1 wherein the compound is 2-(4-fluorophenylmethyl)-1-naphthol.

7. The composition of claim 1 wherein the compound is 2-(4-methoxyphenylmethyl)-1-naphthol.

8. The composition of claim 1 wherein the compound is 2-(3-methoxyphenylmethyl)-1-naphthol.

9. The composition of claim 1 wherein the compound is 2-(4-methylthiophenylmethyl)-1-naphthol.

10. The composition of claim 1 wherein the compound is 2-(4-(N,N-dimethylamino)phenylmethyl)-1-naphthol.

11. The composition of claim 1 wherein the compound is 2-(3-trifluoromethylphenylmethyl)-1-naphthol.

12. The composition of claim 1 wherein the compound is 2-(phenylmethyl)-1-naphthol.

13. The composition of claim 1 wherein the compound is 2-(3-fluorophenylmethyl)-1-naphthol.

14. The composition of claim 1 wherein the compound is 2-[(3,4,5-trimethoxyphenyl)methyl]-1-naphthol.

15. the composition of claim 1 wherein the compound is 2-[(3,4-dimethoxyphenyl)methyl]-1-naphthol.

16. The composition of claim 1 wherein the compound is 2-(3-chlorophenylmethyl)-1-naphthol.

17. The composition of claim 1 wherein the compound is 2-(4-ethoxyphenylmethyl)-1-naphthol.

18. The composition of claim 1 wherein the compound is 2-(4-bromophenylmethyl)-1-naphthol.

19. The composition of claim 1 wherein the compound is 5,8-dimethyl-2-(phenylmethyl)-1-naphthol.

20. A method of inhibiting 5-lipoxygenase in a mammal which comprises administering to the mammal an effective amount of a compound defined in claim 1.

21. A method of inhibiting 5-lipoxygenase in a mammal which comprises administering to the mammal an effective amount of a compound defined in claim 2.

22. A method of inhibiting 5-lipoxygenase in a mammal which comprises administering to the mammal an effective amount of a compound defined in claim 3.

23. A method of inhibiting 5-lipoxygenase in a mammal which comprises administering to the mammal an effective amount of a compound defined in claim 4.

24. A method of inhibiting 5-lipoxygenase in a mammal which comprises administering to the mammal an effective amount of a compound defined in claim 5.

25. A method of inhibiting 5-lipoxygenase in a mammal which comprises administering to the mammal an effective amount of a compound defined in claim 6.

26. A method of inhibiting 5-lipoxygenase in a mammal which comprises administering to the mammal an effective amount of a compound defined in claim 7.

27. A method of inhibiting 5-lipoxygenase in a mammal which comprises administering to the mammal an effective amount of a compound defined in claim 8.

28. A method of inhibiting 5-lipoxygenase in a mammal which comprises administering to the mammal an effective amount of a compound defined in claim 9.

29. A method of inhibiting 5-lipoxygenase in a mammal which comprises administering to the mammal an effective amount of a compound defined in claim 10.

30. A method of inhibiting 5-lipoxygenase in a mammal which comprises administering to the mammal an effective amount of a compound defined in claim 11.

31. A method of inhibiting 5-lipoxygenase in a mammal which comprises administering to the mammal an effective amount of a compound defined in claim 12.

32. A method of inhibiting 5-lipoxygenase in a mammal which comprises administering to the mammal an effective amount of a compound defined in claim 13.

33. A method of inhibiting 5-lipoxygenase in a mammal which comprises administering to the mammal an effective amount of a compound defined in claim 14.

34. A method of inhibiting 5-lipoxygenase in a mammal which comprises administering to the mammal an effective amount of a compound defined in claim 15.

35. A method of inhibiting 5-lipoxygenase in a mammal which comprises administering to the mammal an effective amount of a compound defined in claim 16.

36. A method of inhibiting 5-lipoxygenase in a mammal which comprises administering to the mammal an effective amount of a compound defined in claim 17.

37. A method of inhibiting 5-lipoxygenase in a mammal which comprises administering to the mammal an effective amount of a compound defined in claim 18.

38. A method of inhibiting 5-lipoxygenase in a mammal which comprises administering to the mammal an effective amount of a compound defined in claim 19.

39. A compound having the formula:

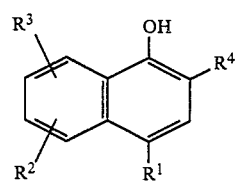

(II)

wherein
$R^1$ is H,
$R^2$ and $R^3$ independently are H, $CH_3$, $C_2H_5$, $CH_3O$, or $C_2H_5O$;
$R^4$ is

$R^7$ is $C_3$–$C_8$ cycloalkyl,

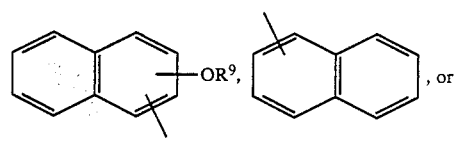

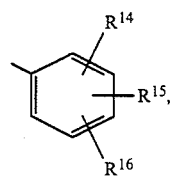

$R^9$ is H or $C_1$–$C_4$ alkyl;
$R^{12}$ and $R^{13}$ independently are H, $C_1$–$C_4$ alkyl, or together are $(CH_2)_{4-5}$;
$R^{14}$ is $C_1$–$C_4$ alkyl, $OR^9$, O-phenyl, O-benzyl, $CF_3$, Cl, Br, I, $N(R^{12})(R^{13})$, or $S(O)_wR^9$ where w is 0–2 with the proviso that if w is 1 then $R^9$ is not H; and
$R^{15}$ and $R^{16}$ are independently H, $C_1$–$C_4$ alkyl, $OR^9$, O-benzyl, F or Cl; and
$R^{21}$ is H, subject to the following provisos:
1. if $R^1$, $R^2$, and $R^3$ are all H, then $R^4$ is not 4-chlorophenylmethyl, or 4-methylphenylmethyl; and 2. if $R^2$ or $R^3$ is 6-$OCH_3$, then $R^4$ is not 4-chlorophenylmethyl or 4-methylphenylmethyl.

40. A compound of claim 39 wherein $R^7$ is

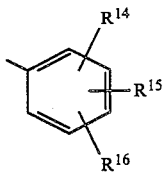

41. A compound of claim 40 wherein
$R^{14}$ is $C_1$–$C_4$ alkyl, $OR^9$, Cl, Br, or I; and
$R^{15}$ and $R^{16}$ are independently H, $OR^9$, .F, or Cl.

42. The compound of claim 39 which is 2-(3-bromophenylmethyl)-1-naphthol.

43. The compound of claim 39 which is 2-(2-fluorophenylmethyl)-1-naphthol.

44. The compound of claim 39 which is 2-(4-fluorophenylmethyl)-1-naphthol.

45. The compound of claim 39 which is 2-(3-fluorophenylmethyl)-1-naphthol.

46. The compound of claim 39 which is 2-[(3,4,5-trimethoxyphenyl)methyl]-1-naphthol.

47. The compound of claim 39 which is 2-[(3,4-dimethoxyphenyl)methyl]-1-naphthol.

48. The compound of claim 39 which is 2-(3-chlorophenylmethyl)-1-naphthol.

49. The compound of claim 39 which is 2-(4-ethoxyphenylmethyl)-1-naphthol.

50. The compound of claim 39 which is 2-(4-bromophenylmethyl)-1-naphthol.

51. The compound of claim 39 which is 5,8-dimethyl-2-(phenylmethyl)-1-naphthol.

* * * * *